US006844446B2

(12) United States Patent
Moody et al.

(10) Patent No.: US 6,844,446 B2
(45) Date of Patent: Jan. 18, 2005

(54) CATALYSTS CONTAINING PER-ORTHO ARYL SUBSTITUTED ARYL OR HETEROARYL SUBSTITUTED NITROGEN DONORS

(75) Inventors: Leslie Shane Moody, Johnson City, TN (US); Peter Borden Mackenzie, Kingsport, TN (US); Christopher Moore Killian, Gray, TN (US); Gino Georges Lavoie, Kingsport, TN (US); James Allen Ponasik, Jr., Blountville, TN (US); Thomas William Smith, Gainesville, FL (US); Jason Clay Pearson, Kingsport, TN (US); Anthony Gerard Martin Barrett, Chiswick (GB)

(73) Assignee: Eastman Chemical Company, Kingsport, TN (US)

(*) Notice: Subject to any disclaimer, the term of this patent is extended or adjusted under 35 U.S.C. 154(b) by 14 days.

(21) Appl. No.: 10/413,150

(22) Filed: Apr. 15, 2003

(65) Prior Publication Data

US 2003/0228978 A1 Dec. 11, 2003

Related U.S. Application Data

(60) Division of application No. 09/942,877, filed on Aug. 31, 2001, now Pat. No. 6,579,823, which is a continuation-in-part of application No. 09/507,492, filed on Feb. 18, 2000, now Pat. No. 6,559,091, and a continuation-in-part of application No. 09/563,812, filed on May 3, 2000, now Pat. No. 6,545,108.
(60) Provisional application No. 60/231,920, filed on Sep. 11, 2000.

(51) Int. Cl.[7] ............................................. C07D 339/02
(52) U.S. Cl. .................... 548/523; 564/271; 564/272; 564/273
(58) Field of Search .................. 548/523; 564/271, 564/272, 273

(56) References Cited

U.S. PATENT DOCUMENTS

| | | |
|---|---|---|
| 4,564,647 A | 1/1986 | Hayashi et al. |
| 4,724,273 A | 2/1988 | Fink et al. |
| 4,752,597 A | 6/1988 | Turner |
| 5,106,804 A | 4/1992 | Bailly et al. |
| 5,132,380 A | 7/1992 | Stevens et al. |
| 5,227,440 A | 7/1993 | Canich et al. |
| 5,296,565 A | 3/1994 | Ueda et al. |
| 5,324,800 A | 6/1994 | Welborn, Jr. et al. |
| 5,331,071 A | 7/1994 | Kataoka et al. |
| 5,332,706 A | 7/1994 | Nowlin et al. |
| 5,350,723 A | 9/1994 | Neithamer et al. |
| 5,399,635 A | 3/1995 | Neithamer et al. |
| 5,466,766 A | 11/1995 | Patsidis et al. |
| 5,468,702 A | 11/1995 | Jejelowo |
| 5,474,962 A | 12/1995 | Takahashi et al. |
| 5,578,537 A | 11/1996 | Herrmann et al. |
| 5,863,853 A | 1/1999 | Vaughan et al. |
| 5,866,663 A | 2/1999 | Brookhart et al. |
| 5,880,241 A | 3/1999 | Brookhart et al. |
| 5,880,323 A | 3/1999 | Brookhart, III et al. |
| 5,886,224 A | 3/1999 | Brookhart et al. |
| 5,891,963 A | 4/1999 | Brookhart et al. |
| 6,197,715 B1 | 3/2001 | Bansleben et al. |
| 6,403,738 B1 | 6/2002 | Johnson et al. |
| 6,407,188 B1 | 6/2002 | Guan et al. |
| 6,410,768 B1 | 6/2002 | Liatas et al. |
| 6,451,939 B1 | 9/2002 | Britovsek et al. |
| 6,545,108 B1 * | 4/2003 | Moody et al. ............... 526/161 |
| 6,559,091 B1 * | 5/2003 | Moody et al. ............... 502/167 |
| 6,579,823 B2 * | 6/2003 | Moody et al. ............... 502/167 |
| 6,706,891 B2 * | 3/2004 | Ponasik et al. ............. 548/523 |

FOREIGN PATENT DOCUMENTS

| | | |
|---|---|---|
| DE | 19707236 A1 | 8/1998 |
| DE | 19944993 A1 | 7/1999 |
| DE | 19959251 A1 | 12/1999 |
| EP | 0 381 495 A2 | 8/1990 |
| EP | 0 416 815 A2 | 3/1991 |
| EP | 0 420 436 A1 | 4/1991 |
| EP | 0 532 098 A1 | 3/1993 |
| EP | 0 641 804 A2 | 3/1995 |
| EP | 0 816 384 A2 | 1/1998 |
| EP | 0 874 005 A1 | 10/1998 |
| EP | 0 884 331 A2 | 12/1998 |
| EP | 0 893 455 A1 | 1/1999 |
| EP | 1 099 714 A1 | 11/1999 |

(List continued on next page.)

OTHER PUBLICATIONS

A. Bach, et al., "Metal Chelated of N–(1– Pyrrolyllsalicyladmines and Their Structure Determination by X–Ray Structure Analysis and X–Ray Absorption Spectroscopy (XANES)," Z. Naturforsch., Chem. Sci., 1996, pp. 757–764, vol. 51(6).

A. V. Bordunov, et al., "Azacrown Ethers Containing Oximic and Schiff Base Sidearms—Potential Heteronuclear Metal Ion Receptors," Tetrahedron, NL, Dec. 29, 1997, pp. 17595–17606, vol. 53, No. 52, Elsevier Science Publishers, Amsterdam.

(List continued on next page.)

Primary Examiner—Mark L. Bell
Assistant Examiner—J. Pasterczyk
(74) Attorney, Agent, or Firm—Bernard J. Graves, Jr.; Jonathan D. Wood

(57) ABSTRACT

Catalyst compositions useful for the polymerization of olefins are disclosed. These compositions comprise a Group 8–10 metal complex comprising a bidentate or variable denticity ligand comprising one or two nitrogen donor atom or atoms independently substituted by an aromatic or heteroaromatic ring(s), wherein the ortho positions of said ring(s) are substituted by aryl or heteroaryl groups. Also disclosed are processes for the polymerization of olefins using the catalyst compositions.

2 Claims, No Drawings

FOREIGN PATENT DOCUMENTS

| | | |
|---|---|---|
| JP | 10-324709 | 3/1997 |
| JP | Hei 9-255712 | 9/1997 |
| JP | Hei 9-272709 | 10/1997 |
| JP | Hei 9-272713 | 10/1997 |
| WO | 94/01471 | 1/1994 |
| WO | 94/11410 | 5/1994 |
| WO | 94/14854 | 7/1994 |
| WO | 96/23010 | 8/1996 |
| WO | 97/02298 | 1/1997 |
| WO | 97/17380 | 5/1997 |
| WO | 97/38024 | 10/1997 |
| WO | 97/48735 | 12/1997 |
| WO | 97/48736 | 12/1997 |
| WO | 97/48737 | 12/1997 |
| WO | 97/48739 | 12/1997 |
| WO | 97/48740 | 12/1997 |
| WO | 97/48742 | 12/1997 |
| WO | 97/48777 | 12/1997 |
| WO | 98/03559 | 1/1998 |
| WO | 98/11144 | 3/1998 |
| WO | 98/27124 | 6/1998 |
| WO | 98/30609 | 7/1998 |
| WO | 98/30610 | 7/1998 |
| WO | 98/37110 | 8/1998 |
| WO | 98/40374 | 9/1998 |
| WO | 98/40420 | 9/1998 |
| WO | 98/40421 | 9/1998 |
| WO | 98/41529 | 9/1998 |
| WO | 98/42664 | 10/1998 |
| WO | 98/42665 | 10/1998 |
| WO | 98/47933 | 10/1998 |
| WO | 98/47934 | 10/1998 |
| WO | 98/56832 | 12/1998 |
| WO | 99/02472 | 1/1999 |
| WO | 99/02570 | 1/1999 |
| WO | 00/47592 A1 | 2/1999 |
| WO | 99/05189 | 2/1999 |
| WO | 99/09078 | 2/1999 |
| WO | 00/58320 A1 | 3/1999 |
| WO | 99/10391 | 3/1999 |
| WO | 99/12981 | 3/1999 |
| WO | 01/07491 A1 | 7/1999 |
| WO | 01/12684 A1 | 8/1999 |
| WO | 01/07492 A1 | 9/1999 |
| WO | 01/14391 A1 | 9/1999 |
| WO | 01/21586 A1 | 9/1999 |
| WO | 01/23396 A1 | 9/1999 |
| WO | 01/42257 A1 | 12/1999 |
| WO | 00/04057 | 1/2000 |
| WO | 01/55231 A1 | 1/2000 |
| WO | 00/50470 A | 8/2000 |
| WO | 01/92342 | 12/2001 |

OTHER PUBLICATIONS

M. Brookhart et al., *J. Am. Chem. Soc.*, 1995, pp. 6414–6415, 117.

Buelow, "Chemische Berichte," *Bericht Der Deutschen Chemischen Gesellschaft, DE, Verlag Chemie. Weinheim*, 1905, pp. 3915, 3917, vol. 38.

R. M. Claramunt, et al., "Rhodium (I) Complexes with the Polydentate Ligand 3,5–bis(4–methylpyrazol–1–yl)–4–methylpyrazole," *Journal Organometallic Chemistry*, 1991, pp. 259–271, vol. 412, No. 1–2.

I. O. Fritsky, et al., "Template Synthesis of Square–Planar Nickel (II) and Copper (III) Complexes Based on Hydrazide Ligands," *J. Chem. Soc., Dalton Trans.*, 1998, pp. 3269–3274, vol. 19.

V. C. Gibson et al., *Chem. Commun.*, 1998, pp. 313–314.

S. D. Ittel et al., "Late–Metal Catalysts for Ethylene Homo– and Copolymerization," *Chem. Rev.*, 2000, pp. 1169–1203, 100.

W. Keim et al,. *Angew Chem. Int. Ed. Engl.*, 1981, pp. 116–117, 20.

D. H. McConville et al., *J. Am. Chem. Soc.*, 1996, pp. 10008–10009, 118.

V. M. Mohring et al., *Angnew. Chem. Int. Ed. Engl.*, 1985, pp. 1001–1003, 24.

K. K. Narang, et al., Glyoxal–Aroyl Hydrazone (Schiff Base) Complexes of Nickel (III), Copper (II) & Zinc (II), *Indian J. Chem., Sect. A.*, 1982, pp. 830–832, vol. 21A(B).

K. K. Narang, et al., "Synthesis, Characterization, Thermal Studies and Biological Activity of Iron (III) Complexes with Some Acylhydrazines," *Synth. React. Inorg. Met.–Org. Chem.*, 1993, pp. 971–989, vol. 23(6).

F. A. Neugebauer, "ESR Studies of 1,2,4,5–Tetraazapentenyls," *Chem. Ber.*, 1973, pp. 1716–1723, vol. 106(6).

M. Peuckert et al., *Organometallics*, 1983, pp. 694–597, 2.

S. B. Roscoe et al., "Polyolefin Spheres from Metallocenes Supported on Noninteracting Polystyrene," *Science*, 1998, pp. 270–273, 280.

L. Rosenberg, et al., "Binuclear Nickel (II) and Cobalt (II) Complexes of the Novel Binucleating Ligand 3,–Bis(1'–pyrazolyl)pyridazine. Crystal and Molecular Structure and Magnetism of Bis($\mu$–3, 6–bis(1'–pyrazolyl)pyridazine–N$^1$(Ni$^1$)N$^2$(Ni$^1$)N$^{21}$(Ni$^1$)N$^2$ (Ni$^2$)N$^2$(Ni$^2$)–bis (diaquanickel (I) Tetrachloride Dihydrate," *J. Chem. Soc., Dalton Trans.*, 1986, pp. 625–631, vol. 3.

M. Schmid et al., "New C$_{2/}$ and Chiral C$_2$–Symmetric Olefin Polymerization Catalysts Based on Nickel (II) and Palladium (II) Diimine Complexes Bearing 2,6–Diphenyl Aniline Moieties: Synthesis, Structural Characterization, and First Insight into Polymerization Properties," *Organometallics*, 2001, 20(11), 2321.

R. R. Schrock et al., *J. Am. Chem. Soc.*, 1997, pp. 3830–3831, 119.

R. R. Schrock et al., *J. Am. Chem. Soc.*, 1999, pp. 5797–5798, 121.

S. H. Strauss, *Chem. Rev.*, 1993, pp. 927–942, 93.

A. A. Watson, et al., "Chiral Heterocyclic Ligands. VIII. Syntheses and Complexes of New Chelating Ligands Derived from Camphor," *Aust. J. Chem.*, 1995, pp. 1549–1572, vol. 48, No. 9.

Oleg v. Mikhailov, "From Novel Complexing Conditions to Novel Coordination Compounds of Nickel (II) with Dithiooxamide and its Bulky Analogues," *Transition Met. Chem.*, (1996), 363–369, 21.

U.S. 2002/0082366 A1, U.S. Pre–Grant Publication to Johnson et al., Jun. 27, 2002.

Timo Repo et al. "Ethylenebis (Salicylidenetiminato) zirconium Dichloride: Crystal Structure and Use as a Heterogeneous Catalyst in the Polymerization of Ethylene", *Maromolecules*, (1977), 171–175, 30.

* cited by examiner

CATALYSTS CONTAINING PER-ORTHO ARYL SUBSTITUTED ARYL OR HETEROARYL SUBSTITUTED NITROGEN DONORS

CROSS REFERENCE TO RELATED APPLICATIONS

This application claims the benefit of Provisional Application No. 60/231,920, filed on Sep. 11, 2000, under 35 USC §119; the entire content of which is hereby incorporated by reference.

This application is a divisional of application Ser. No. 09/942,877, filed on Aug. 31, 2001 now U.S. Pat. No. 6,579,823, which is a continuation-in-part of application Ser. Nos. 09/507,492 filed on Feb. 18, 2000 now U.S. Pat. No. 6,559,091, and Ser. No. 09/563,812, filed on May 3, 2000 now U.S. Pat. No. 6,545,108, the entire content of both applications is hereby incorporated by reference.

FIELD OF THE INVENTION

The present invention generally relates to catalyst compositions useful for the polymerization or oligomerization of olefins, and to processes using the catalyst compositions. Certain of these catalyst compositions comprise a Group 8–10 metal complex comprising a bidentate or variable denticity ligand comprising one or two nitrogen donor atom or atoms independently substituted by an aromatic or heteroaromatic ring(s), wherein the ortho positions of said ring(s) are substituted by aryl or heteroaryl groups.

BACKGROUND OF THE INVENTION

Olefin polymers are used in a wide variety of products, from sheathing for wire and cable to film. Olefin polymers are used, for instance, in injection or compression molding applications, in extruded films or sheeting, as extrusion coatings on paper, for example photographic paper and digital recording paper, and the like. Improvements in catalysts have made it possible to better control polymerization processes and, thus, influence the properties of the bulk material. Increasingly, efforts are being made to tune the physical properties of plastics for lightness, strength, resistance to corrosion, permeability, optical properties, and the like, for particular uses. Chain length, polymer branching and functionality have a significant impact on the physical properties of the polymer. Accordingly, novel catalysts are constantly being sought in attempts to obtain a catalytic process for polymerizing olefins which permits more efficient and better-controlled polymerization of olefins.

The use of late transition metal complexes as catalysts for olefin polymerization has recently been reviewed by Ittel et al. (*Chem. Rev.* 2000, 100, 1169). Notwithstanding the many advances described therein, there remains a need for new late transition metal catalysts and processes with improved productivities under the elevated temperatures and pressures of commercial reactor operating conditions. New catalysts and processes for these purposes are described herein.

SUMMARY OF THE INVENTION

In a first aspect, this invention relates to a catalyst composition useful for the polymerization of olefins, which comprises a Group 8–10 metal complex comprising a bidentate or variable denticity ligand comprising two nitrogen donor atoms independently substituted by aromatic or heteroaromatic rings, wherein the ortho positions of the rings are substituted by aryl or heteroaryl groups.

In a second aspect, this invention relates to a catalyst composition comprising either (i) a compound of formula ee1, (ii) the reaction product of a metal complex of formula ff1 and a second compound $Y^1$, or (iii) the reaction product of $Ni(1,5\text{-cyclooctadiene})_2$, $B(C_6F_5)_3$, a ligand selected from Set 18, and optionally an olefin;

Set 18

$$[(L^2)Ni(T)(L)]^+X^-$$  ee1

$$(L^2)Ni(Q)(W^1)$$  ff1

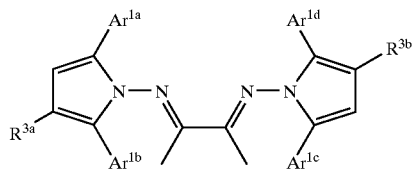

gg1

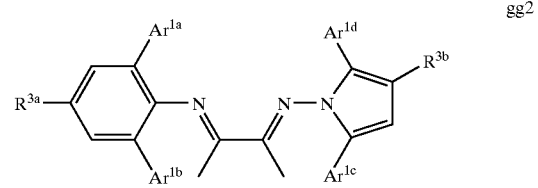

gg2

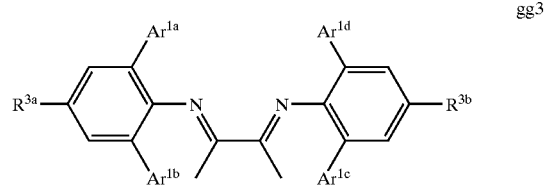

gg3

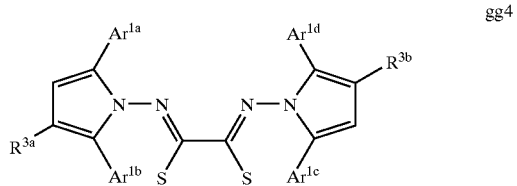

gg4

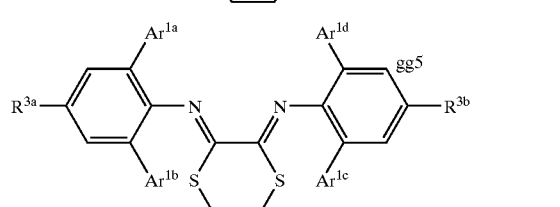

gg5

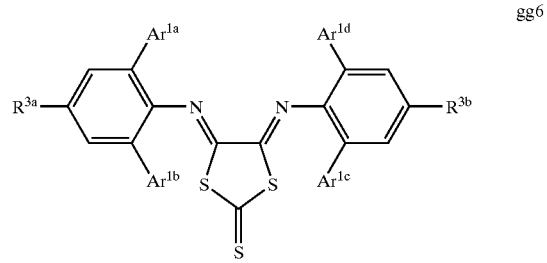

gg6

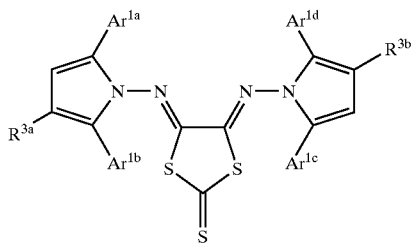

wherein:

L² is selected from Set 18;

T is H, hydrocarbyl, substituted hydrocarbyl, or other group capable of inserting an olefin;

L is an olefin or a neutral donor group capable of being displaced by an olefin; in addition, T and L may be taken together to form a π-allyl or π-benzyl group;

X⁻ is $BF_4^-$, $B(C_6F_5)_4^-$, $BPh_4^-$, or another weakly coordinating anion;

Q and $W^1$ are each independently fluoro, chloro, bromo or iodo, hydrocarbyl, substituted hydrocarbyl, heteroatom attached hydrocarbyl, heteroatom attached substituted hydrocarbyl, or collectively sulfate, or may be taken together to form a π-allyl, π-benzyl, or acac group, in which case a weakly coordinating counteranion X⁻ is also present;

$Y^1$ is either (i) a metal hydrocarbyl capable of abstracting acac ff1 in exchange for alkyl or another group capable of inserting an olefin, (ii) a neutral Lewis acid capable of abstracting Q⁻ or $W^{1-}$ from ff1 to form a weakly coordinating anion, cationic Lewis acid whose counterion is a weakly coordinating anion, or a Bronsted acid whose conjugate base is a weakly coordinating anion, or (iii) a Lewis acid capable of reacting with a π-allyl or π-benzyl group, or a substituent thereon, in ff1 to initiate olefin polymerization;

$R^{3a,b}$ are each independently H, alkyl, hydrocarbyl, substituted hydrocarbyl, 2,4,6-triphenylphenyl, heteroatom connected hydrocarbyl, heteroatom connected substituted hydrocarbyl, or fluoroalkyl; and $Ar^{1a-d}$ are each independently phenyl, 4-alkylphenyl, 4-tert-butylphenyl, 4-trifluoromethylphenyl, 4-hydroxyphenyl, 4-(heteroatom attached hydrocarbyl)-phenyl, 4-(heteroatom attached substituted hydrocarbyl)-phenyl, or 1-naphthyl.

In a first preferred embodiment of this second aspect, the metal complex of formula ff1 is selected from Set 19;

Set 19

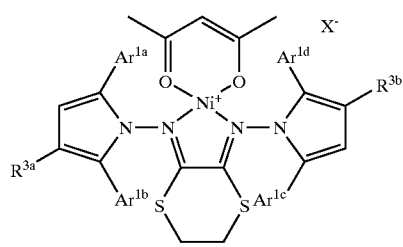

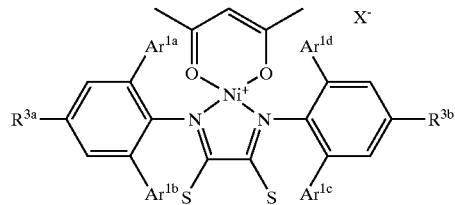

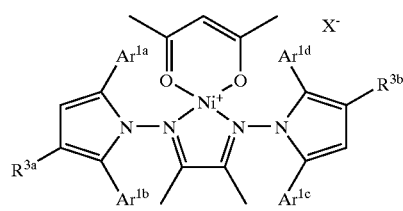

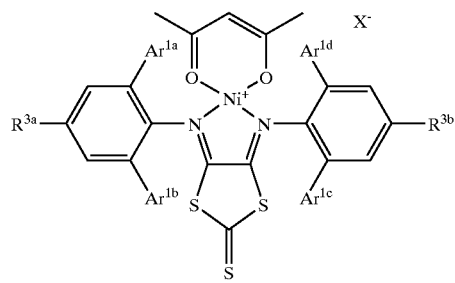

wherein:
$R^{3a,b}$ are each independently H, methyl, phenyl, 4-methoxyphenyl, or 4-tert-butylphenyl;
$Ar^{1a-d}$ are each independently phenyl, 4-methylphenyl, 4-tert-butylphenyl, 4-trifluoromethylphenyl, 1-naphthyl, 2-naphthyl, or 4-phenylphenyl; and
X⁻ is $BF_4^-$, $B(C_6F_5)_4^-$, $BPh_4^-$, or another weakly coordinating anion.

In a second preferred embodiment of this second aspect, the substituents $Ar^{1a-d}$ are 4-tert-butylphenyl or 1-naphthyl. In a third, especially preferred, embodiment, the catalyst composition further comprises a solid support.

In a third aspect, this invention relates to a process for the polymerization of olefins, comprising contacting one or more olefins with the catalyst composition of the second aspect. In a preferred embodiment, of this second aspect, the second compound $Y^1$ is trimethylaluminum, and the metal complex is contacted with the trimethylaluminum in a gas phase olefin polymerization reactor.

In a fourth aspect, this invention relates to a compound of formula ii1;

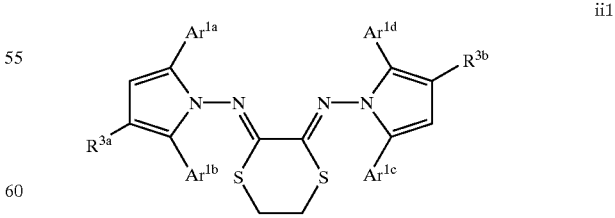

wherein:
$R^{3a,b}$ are each independently H, methyl, phenyl, 4-methoxyphenyl, or 4-tert-butylphenyl; and
$Ar^{1a-d}$ are each independently phenyl, 4-methylphenyl, 4-tert-butylphenyl, 4-trifluoromethylphenyl, 1-naphthyl, 2-naphthyl, or 4-phenylphenyl. Compounds of this formula are useful as ligands in constituting the catalysts of the present invention.

In a fifth aspect, the invention relates to a process for the polymerization of olefins, comprising contacting one or more olefins with a catalyst composition comprising a Group 8–10 transition metal complex which comprises a ligand selected from Set 20;

Set 20

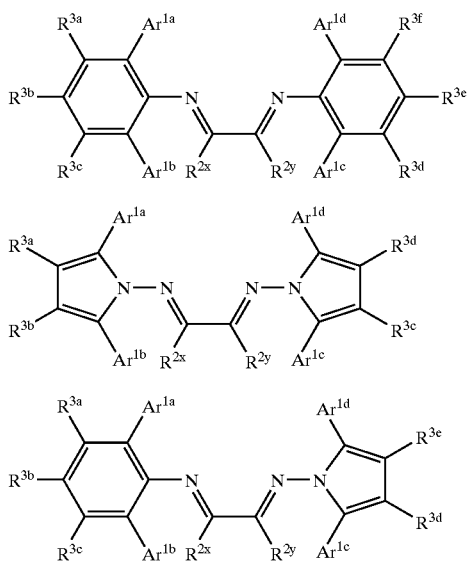

wherein:

$R^{2x,y}$ are each independently H, hydrocarbyl, substituted hydrocarbyl, heteroatom connected hydrocarbyl, or heteroatom connected substituted hydrocarbyl; in addition, $R^{2x}$ and $R^{2y}$ may be linked by a bridging group;

$R^{3a-f}$ are each independently H, alkyl, hydrocarbyl, substituted hydrocarbyl, heteroatom connected hydrocarbyl, heteroatom connected substituted hydrocarbyl, or fluoroalkyl; and $Ar^{1a-d}$ are each independently phenyl, 4-alkylphenyl, 4-tert-butylphenyl, 4-trifluoromethylphenyl, 4-hydroxyphenyl, 4-(heteroatom attached hydrocarbyl)-phenyl, 4-(heteroatom attached substituted hydrocarbyl)-phenyl, 1-naphthyl, 2-naphthyl, 9-anthracenyl, or aryl.

In a sixth aspect, this invention relates to a compound selected from Set 21;

Set 21

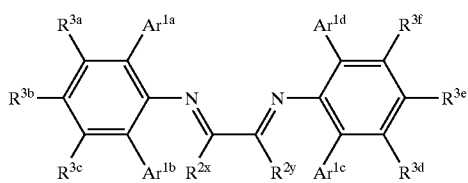

-continued

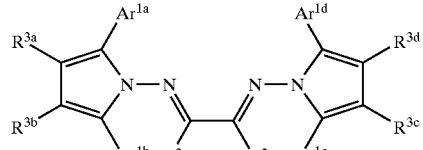

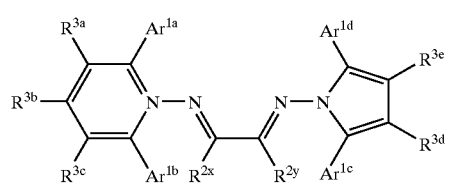

wherein:

$R^{2x,y}$ are each independently H, hydrocarbyl, substituted hydrocarbyl, heteroatom connected hydrocarbyl, or heteroatom connected substituted hydrocarbyl; in addition, $R^{2x}$ and $R^{2y}$ may be linked by a bridging group;

$R^{3a-f}$ are each independently H, alkyl, hydrocarbyl, substituted hydrocarbyl, heteroatom connected hydrocarbyl, heteroatom connected substituted hydrocarbyl, or fluoroalkyl; and $Ar^{1a-d}$ are each independently phenyl, 4-alkylphenyl, 4-tert-butylphenyl, 4-trifluoromethylphenyl, 4-hydroxyphenyl, 4-(heteroatom attached hydrocarbyl)-phenyl, 4-(heteroatom attached substituted hydrocarbyl)-phenyl, 1-naphthyl, 2-naphthyl, 9-anthracenyl, or aryl. These compounds are are useful as ligands in constituting the catalysts of the present invention.

In a seventh aspect, this invention relates to a catalyst composition useful for the polymerization of olefins, which comprises a Group 8–10 transition metal complex comprising a N,N-donor ligand of the formula kk1 or kk2;

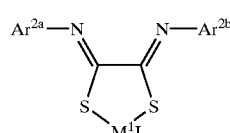

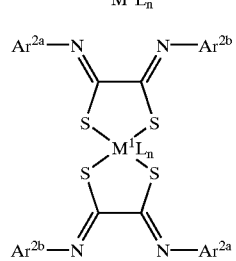

wherein:

$Ar^{2a,b}$ are each independently aromatic or heteroaromatic groups wherein the ortho positions are substituted by aryl or heteroaryl groups;

$M^1$ is a metal selected from Groups 3, 4, 5, 6, 13, or 14, or is Cu, P or As; and $L_n$ are ancillary ligands or groups which satisfy the valency of $M^1$, such that $M^1$ is either a neutral, monoanionic or cationic metal center, or is a neutral or cationic P or As, with suitable counterions such that said catalyst composition has no net charge. $M^1L_n$ may also be an active site for olefin polymerization. The compounds of formula kk2 are capable of ligating to two Group 8–10 metal centers, which may be the same or different, where one or both of said Group 8–10 metal centers may be active sites for olefin polymerization.

In an eighth aspect, this invention relates to a process for the polymerization of olefins, comprising contacting one or more olefins with the catalyst composition the seventh aspect.

We have surprisingly found that the catalyst compositions of the present invention can provide improved stability in the presence of an amount of hydrogen effective to achieve chain transfer, a total productivity greater than about 28,000 kg polyethylene per mole of catalyst at an operating temperature of at least 60° C. (preferably greater than 56,000 kg PE/mol catalyst), and/or a higher productivity in the presence of an amount of hydrogen effective to achieve chain transfer, relative to the productivity observed in the absence of hydrogen.

DETAILED DESCRIPTION OF THE INVENTION

In this disclosure, symbols ordinarily used to denote elements in the Periodic Table and commonly abbreviated groups, take their ordinary meaning, unless otherwise specified. Thus, N, O, S, P, and Si stand for nitrogen, oxygen, sulfur, phosphorus, and silicon, respectively, while Me, Et, Pr, $^i$Pr, Bu, $^t$Bu and Ph stand for methyl, ethyl, propyl, iso-propyl, butyl, tert-butyl and phenyl, respectively.

A "hydrocarbyl" group means a monovalent or divalent, linear, branched or cyclic group which contains only carbon and hydrogen atoms. Examples of monovalent hydrocarbyls include the following: $C_1$–$C_{20}$ alkyl; $C_1$–$C_{20}$ alkyl substituted with one or more groups selected from $C_1$–$C_{20}$ alkyl, $C_3$–$C_8$ cycloalkyl, and aryl; $C_3$–$C_8$ cycloalkyl; $C_3$–$C_8$ cycloalkyl substituted with one or more groups selected from $C_1$–$C_{20}$ alkyl, $C_3$–$C_8$ cycloalkyl, and aryl; $C_6$–$C_{14}$ aryl; and $C_6$–$C_{14}$ aryl substituted with one or more groups selected from $C_1$–$C_{20}$ alkyl, $C_3$–$C_8$ cycloalkyl, and aryl. Examples of divalent (bridging) hydrocarbyls include: —$CH_2$—, —$CH_2CH_2$—, —$CH_2CH_2CH_2$—, and 1,2-phenylene.

The term "aryl" refers to an aromatic carbocyclic monoradical, which may be substituted or unsubstituted, wherein the substituents are halo, hydrocarbyl, substituted hydrocarbyl, heteroatom attached hydrocarbyl, heteroatom attached substituted hydrocarbyl, nitro, cyano, fluoroalkyl, sulfonyl, and the like. Examples include: phenyl, naphthyl, anthracenyl, phenanthracenyl, 2,6-diphenylphenyl, 3,5-dimethylphenyl, 4-nitrophenyl, 3-nitrophenyl, 4-methoxyphenyl, 4-dimethylaminophenyl, and the like.

A "heterocyclic ring" refers to a carbocyclic ring wherein one or more of the carbon atoms has been replaced by an atom selected from the group consisting of O, N, S, P, Se, As, Si, B, and the like.

A "heteroaromatic ring" refers to an aromatic heterocycle; examples include pyrrole, furan, thiophene, indene, imidazole, oxazole, isoxazole, carbazole, thiazole, pyrimidine, pyridine, pyridazine, pyrazine, benzothiophene, and the like.

A "heteroaryl" refers to a heterocyclic monoradical which is aromatic; examples include 1-pyrrolyl, 2-pyrrolyl, 3-pyrrolyl, furyl, thienyl, indenyl, imidazolyl, oxazolyl, isoxazolyl, carbazolyl, thiazolyl, pyrimidinyl, pyridyl, pyridazinyl, pyrazinyl, benzothienyl, and the like, and substituted derivatives thereof.

A "silyl" group refers to a $SiR_3$ group wherein Si is silicon and R is hydrocarbyl or substituted hydrocarbyl or silyl, as in $Si(SiR_3)_3$.

A "boryl" group refers to a $BR_2$ or $B(OR)_2$ group, wherein R is hydrocarbyl or substituted hydrocarbyl.

A "heteroatom" refers to an atom other than carbon or hydrogen. Preferred heteroatoms include oxygen, nitrogen, phosphorus, sulfur, selenium, arsenic, chlorine, bromine, silicon, and fluorine.

A "substituted hydrocarbyl" refers to a monovalent, divalent, or trivalent hydrocarbyl substituted with one or more heteroatoms. Examples of monovalent substituted hydrocarbyls include: 2,6-dimethyl-4-methoxyphenyl, 2,6-diisopropyl-4-methoxyphenyl, 4-cyano-2,6-dimethylphenyl, 2,6-dimethyl-4-nitrophenyl, 2,6-difluorophenyl, 2,6-dibromophenyl, 2,6-dichlorophenyl, 4-methoxycarbonyl-2,6-dimethylphenyl, 2-tert-butyl-6-chlorophenyl, 2,6-dimethyl-4-phenylsulfonylphenyl, 2,6-dimethyl-4-trifluoromethylphenyl, 2,6-dimethyl-4-trimethylammoniumphenyl (associated with a weakly coordinated anion), 2,6-dimethyl-4-hydroxyphenyl, 9-hydroxyanthr-10-yl, 2-chloronapth-1-yl, 4-methoxyphenyl, 4-nitrophenyl, 9-nitroanthr-10-yl, —$CH_2OCH_3$, cyano, trifluoromethyl, and fluoroalkyl. Examples of divalent (bridging) substituted hydrocarbyls include: 4-methoxy-1,2-phenylene, 1-methoxymethyl-1,2-ethanediyl, 1,2-bis(benzyloxymethyl)-1,2-ethanediyl, and 1-(4-methoxyphenyl)-1,2-ethanediyl. Examples of trivalent hydrocarbyls include methine and phenyl-substituted methane.

A "heteroatom connected hydrocarbyl" refers to a group of the type $E^{10}$(hydrocarbyl), $E^{20}$H(hydrocarbyl), or $E^{20}$(hydrocarbyl)$_2$, where $E^{10}$ is an atom selected from Group 16 and $E^{20}$ is an atom selected from Group 15.

A "heteroatom connected substituted hydrocarbyl" refers to a group of the type $E^{10}$(substituted hydrocarbyl), $E^{20}$H (substituted hydrocarbyl), or $E^{20}$(substituted hydrocarbyl)$_2$, where $E^{10}$ is an atom selected from Group 16 and $E^{20}$ is an atom selected from Group 15.

The term "fluoroalkyl" as used herein refers to a $C_1$–$C_{20}$ alkyl group substituted by one or more fluorine atoms.

An "olefin" refers to a compound of the formula $R^{1a}CH=CHR^{1b}$, where $R^{1a}$ and $R^{1b}$ may independently be H, hydrocarbyl, substituted hydrocarbyl, fluoroalkyl, silyl, O(hydrocarbyl), or O(substituted hydrocarbyl), and where $R^{1a}$ and $R^{1b}$ may be connected to form a cyclic olefin, provided that in all cases, the substituents $R^{1a}$ and $R^{1b}$ are compatible with the catalyst. In the case of most Group 4–7 catalysts, this will generally mean that the olefin should not contain good Lewis base donors, since this will tend to severely inhibit catalysis. Preferred olefins for such catalysts include ethylene, propylene, butene, hexene, octene, cyclopentene, norbornene, and styrene.

In the case of the Group 8–10 catalysts, Lewis basic substituents on the olefin will tend to reduce the rate of catalysis in most cases; however, useful rates of homopolymerization or copolymerization can nonetheless be achieved with some of those olefins. Preferred olefins for such catalysts include ethylene, propylene, butene, hexene, octene, and fluoroalkyl substituted olefins, but may also include, in the case of palladium and some of the more functional group tolerant nickel catalysts, norbornene, substituted norbornenes (e.g., norbornenes substituted at the 5-position with halide, siloxy, silane, halo carbon, ester, acetyl, alcohol, or amino groups), cyclopentene, ethyl undecenoate, acrylates, vinyl ethylene carbonate, 4-vinyl-2, 2-dimethyl-1,3-dioxolane, and vinyl acetate.

In some cases, the Group 8–10 catalysts can be inhibited by olefins which contain additional olefinic or acetylenic functionality. This is especially likely if the catalyst is prone to "chain-running" wherein the catalyst can migrate up and down the polymer chain between insertions, since this can lead to the formation of relatively unreactive π-allylic intermediates when the olefin monomer contains additional unsaturation. Such effects are best determined on a case-by-case basis, but may be predicted to some extent through knowledge of how much branching is observed with a given catalyst in ethylene homopolymerizations; those catalysts which tend to give relatively high levels of branching with ethylene will tend to exhibit lower rates when short chain diene co-monomers are used under the same conditions. Longer chain dienes tend to be less inhibitory than shorter chain dienes, when other factors are kept constant, since the catalyst has farther to migrate to form the π-allyl, and another insertion may intervene first.

Similar considerations apply to unsaturated esters which are capable of inserting and chain-running to form relatively stable intramolecular chelate structures wherein the Lewis basic ester functionality occupies a coordination site on the catalyst. In such cases, short chain unsaturated esters, such as methyl acrylate, tend to be more inhibitory than long chain esters, such as ethyl undecenoate, if all other factors are kept constant.

A "π-allyl" group refers to a monoanionic group with three $sp^2$ carbon atoms bound to a metal center in a $\eta^3$-fashion. Any of the three $sp^2$ carbon atoms may be substituted with a hydrocarbyl, substituted hydrocarbyl, heteroatom connected hydrocarbyl, heteroatom connected substituted hydrocarbyl, or O-silyl group. Examples of π-allyl groups include:

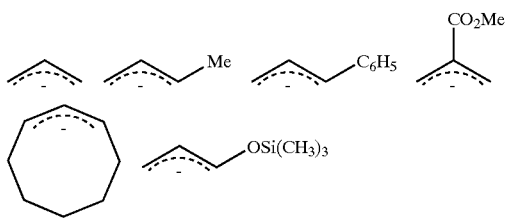

The term π-benzyl group denotes an π-allyl group where two of the $sp^2$ carbon atoms are part of an aromatic ring. Examples of π-benzyl groups include:

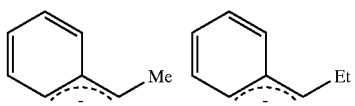

A "bridging group" refers to an atom or group which links two or more groups, which has an appropriate valency to satisfy its requirements as a bridging group, and which is compatible with the desired catalysis. Suitable examples include divalent or trivalent hydrocarbyl, substituted hydrocarbyl, heteroatom connected hydrocarbyl, heteroatom connected substituted hydrocarbyl, substituted silicon (IV), boron(III), N(III), P(III), and P(V), —C(O)—, —SO$_2$—, —C(S)—, —B(OMe)—, —C(O)C(O)—, O, S, and Se. In some cases, the groups which are said to be "linked by a bridging group" are directly bonded to one another, in which case the term "bridging group" is meant to refer to that bond. By "compatible with the desired catalysis," we mean a bridging group or substituent which either does not interfere with the desired catalysis, or acts to usefully modify the catalyst activity or selectivity.

The term "weakly coordinating anion" is well known in the art per se and generally refers to a large bulky anion capable of delocalization of the negative charge of the anion. Weakly coordinating anions, not all of which would be considered bulky, include, but are not limited to: $B(C_6F_5)_4^-$, $PF_6^-$, $BF_4^-$, $SbF_6^-$, $(F_3CSO_2)_2N^-$, $(F_3CSO_2)_3C^-$, $(Ph)_4B^-$ wherein Ph=phenyl, and $Ar_4B^-$ wherein $Ar_4B^-$=tetrakis[3, 5-bis(trifluoromethyl)phenyl]-borate. The weakly coordinating nature of such anions is known and described in the literature (S. Strauss et al., Chem. Rev., 1993, 93, 927).

The term "ortho" is used herein in the context of the ligands of the present invention to denote the positions which are adjacent to the point of attachment of the aromatic or heteroaromatic ring to the ligated nitrogen(s). In the case of a 1-attached, 6-membered ring, we mean the 2- and 6-positions. In the case of a 1-attached, 5-membered ring, we mean the 2- and 5-positions. In the case of 1-attached, fused ring aromatic or heteroaromatic rings, we mean the first positions which can be substituted; for example, in the case of 1-naphthyl, these would be the 2- and 8-positions; in the case of 9-anthracenyl, these would be the 1- and 8-positions.

The term "variable denticity" is used herein in the context of otherwise bidentate ligands to refer to the reversible formation of a third binding interaction between the ligand and the Group 8–10 transition metal center to which it is complexed.

The abbreviation "acac" refers to acetylacetonate. In general, substituted acetylacetonates, wherein one or more hydrogens in the parent structure have been replaced by a hydrocarbyl, substituted hydrocarbyl, or fluoroalkyl, may be used in place of the "acac". Hydrocarbyl substituted acetylacetonates may be preferred in some cases when it is important, for example, to improve the solubility of a (ligand)Ni(acac)BF$_4$ salt in mineral spirits.

The phrase "an amount of hydrogen effective to achieve chain transfer" refers to the ability of hydrogen to react with an olefin polymerization catalyst to cleave off a growing polymer chain and initiate a new chain. In most cases, this is believed to involve hydrogenolysis of the metal-carbon bond of the growing polymer chain, to form a metal hydride catalytic intermediate, which can then react with the olefin monomer to initiate a new chain. In the context of the current invention, an effective amount is considered to be that amount of hydrogen which reduces both the number average molecular weight and the weight average molecular weight of the polymer by at least 10%, relative to an otherwise similar reaction conducted in the absence of hydrogen. In this context, "otherwise similar" denotes that the catalyst, catalyst loading, solvent, solvent volume, agitation, ethylene pressure, co-monomer concentration, reaction time, and other process relevant parameters are sufficiently similar that a valid comparison can be made.

In general, previously reported catalysts lacking the novel ortho-aryl substitution pattern of the current invention are far less productive in the presence of an amount of hydrogen effective to achieve chain transfer than they are under otherwise similar conditions without hydrogen. In order to quantify this effect, the following terms are defined.

The productivity P is defined as the grams of polymer produced per mole of catalyst, over a given period of time. The productivity $P_{hydrogen}$ is defined as the grams of polymer produced per mole of catalyst in the presence of an amount of hydrogen effective to achieve chain transfer, in an otherwise similar reaction conducted for the same period of time. Catalysts lacking the novel ortho-aryl substitution pattern of the catalyst compositions of the current invention typically exhibit ratios $P_{hydrogen}/P$ less than or equal to 0.05 under substantially non-mass transport limited conditions.

The phrase "improved stability in the presence of an amount of hydrogen effective to achieve chain transfer" means that the ratio $P_{hydrogen}/P$ is at least 0.1 under substantially non-mass transport limited conditions. Preferred catalysts of the present invention exhibit a ratio $P_{hydrogen}/P$ greater than or equal to 0.2 under substantially non-mass transport limited conditions. Especially preferred catalysts of the present invention exhibit a ratio $P_{hydrogen}/P$ greater than or equal to 0.5 under substantially non-mass transport limited conditions.

The phrase "one or more olefins" refers to the use of one or more chemically different olefin monomer feedstocks, for example, ethylene and propylene.

The phrase "capable of inserting an olefin" refers to a group Z bonded to the transition metal M, which can insert an olefin monomer of the type $R^{1a}CH=CHR^{1b}$ to form a moiety of the type $M—CHR^{1a}—CHR^{1b}—Z$, which can subsequently undergo further olefin insertion to form a polymer chain; wherein $R^{1a}$ and $R^{1b}$ may independently be H, hydrocarbyl, substituted hydrocarbyl, fluoroalkyl, silyl, O(hydrocarbyl), or O(substituted hydrocarbyl), and wherein $R^{1a}$ and $R^{1b}$ may be connected to form a cyclic olefin, provided that in all cases, the substituents $R^{1a}$ and $R^{1b}$ are compatible with the desired catalysis; wherein additional groups will be bound to the transition metal M to comprise the actual catalyst, as discussed in more detail below.

The degree of steric hindrance at the active catalyst site required to give slow chain transfer, and thus form polymer, depends on a number of factors and is often best determined by experimentation. These factors include: the exact structure of the catalyst, the monomer or monomers being polymerized, whether the catalyst is in solution or attached to a solid support, and the temperature and pressure. The term "polymer" is defined herein as corresponding to a degree of polymerization, DP, of about 10 or more; oligomer is defined as corresponding to a DP of 2 to about 10.

The term "total productivity" is defined in the context of ethylene polymerization as the number of kilograms of polyethylene per mole of catalyst and is the maximum weight of polyethylene that can be produced using a given catalyst.

By "suitable counterions", we mean weakly coordinating ions with sufficient charge to give the overall catalyst complex no net charge.

In the context of structures kk1 and kk2, "ancillary ligands" are atoms or groups which serve to satisfy the valency of $M^1$ without interfering with the desired catalysis.

The compounds of Sets 18–21 and formula ii1 may be prepared as described in the examples contained herein, or by methods described in the references cited by Ittel et al. (*Chem. Rev.* 2000, 100, 1169); or in U.S. patent application Ser. No. 09/507,492, filed on Feb. 18, 2000, Ser. No. 09/563,812, filed on May 3, 2000, and Ser. No. 09/231,920, filed on Sep. 11, 2000; or in U.S. Provisional Application Nos. 60/246,254, 60/246,255, and 60/246,178, all filed on Nov. 6, 2000.

A variety of protocols may be used to generate active polymerization catalysts comprising transition metal complexes of various nitrogen, phosphorous, oxygen and sulfur donor ligands. Examples include: (i) the reaction of a Ni(II), Pd(II), Co(II) or Fe(II) dihalide complex of a bidentate N,N-donor ligand with an alkylaluminum reagent, for example, the reaction of (bidentate N,N-donor ligand)Ni (acac)X salts with an alkylaluminum reagent, where X is a weakly coordinating anion, such as $B(C_6F_5)_4^-$, $BF_4^-$, $PF_6^-$, $SbF_6^-$ and $OS(O)_2CF_3^-$, (ii) the reaction of a bidentate N,N-donor ligand with bis(1,5-cyclooctadiene)nickel(0) and $[H(OEt_2)_2]^+[B(3,5-(CF_3)_2C_6H_3)_4]^-$, and (iii) the reaction of a bidentate N,N-donor ligand with bis(1,5-cyclooctadiene) nickel(0) and $B(C_6F_5)_3$. Cationic [(ligand)M(π-allyl)]$^+$ complexes with weakly coordinating counteranions, where M is a Group 10 transition metal, are often also suitable catalyst precursors, requiring only exposure to olefin monomer and in some cases elevated temperatures (40–100° C.) or added Lewis acid, or both, to form an active polymerization catalyst.

More generally, a variety of (ligand)$_n$M(Z$^{1a}$)(Z$^{1b}$) complexes, where "ligand" refers to a compound of the present invention and is a bidentate or variable denticity ligand comprising one or two nitrogen donor atom or atoms independently substituted by an aromatic or heteroaromatic ring(s), wherein the ortho positions of the ring(s) are substituted by aryl or heteroaryl groups, n is 1 or 2, M is a Group 8–10 transition metal, Z$^{1a}$ and Z$^{1b}$ are univalent groups, or may be taken together to form divalent group, may be reacted with one or more compounds, collectively referred to as compound Y$^1$, which function as co-catalysts or activators, to generate an active catalyst of the form [(ligand) $_n$M(T$^{1a}$)(L)]$^+$X$^-$, where n is 1 or 2, T$^{1a}$ is a hydrogen atom or hydrocarbyl, L is an olefin or neutral donor group capable of being displaced by an olefin, M is a G up 8–10 transition metal, and X$^-$ is a weakly coordinating anion. When Z$^{1a}$ and Z$^{1b}$ are both halide, examples of compound Y$^1$ include: methylaluminoxane (herein MAO) and other aluminum sesquioxides, $R_3Al$, $R_2AlCl$, and $RAlCl_2$ (wherein R is alkyl, and plural groups R may be the same or different). When Z$^{1a}$ and Z$^{1b}$ are both alkyl, examples of a compound Y$^1$ include: MAO and other aluminum sesquioxides, $R_3Al$, $R_2AlCl$, $RAlCl_2$ (wherein R is alkyl, and plural groups R may be the same or different), $B(C_6F_5)_3$, $R^0{}_3Sn[BF_4]$ wherein $R^0$ is hydrocarbyl or substituted hydrocarbyl and plural groups $R^0$ may be the same or different), H$^+$X$^-$, wherein K$^-$ is a weakly coordinating anion for example, tetrakis[3,5-bis(trifluoromethyl)phenyl]borate, and Lewis acidic or Bronsted acidic metal oxides, for example, montmorillonite clay. In some cases, for example, when Z$^{1a}$ and Z$^{1b}$ are both halide or carboxylate, sequential treatment with a metal hydrocarbyl, followed reaction with a Lewis acid, may be required to generate an active catalyst. Examples of metal hydrocarbyls include: MAO, other aluminum sesquioxides, $R_3Al$, $R_2AlCl$, $RAlCl_2$ (wherein R is alkyl, and plural groups R may be the same or different), Grignard reagents, organolithium reagents, and diorganozinc reagents. Examples of Lewis acids include: MAO, other aluminum sesquioxides, $R_3Al$, $R_2AlCl$, $RAlCl_2$ (wherein R is alkyl, and plural groups R may be the same or different), $B(C_6F_5)_3$, $R^0{}_3Sn[BF_4]$ (wherein $R^0$ is hydrocarbyl or substituted hydrocarbyl and plural groups $R^0$ may be the same or different), and Lewis acidic metal oxides.

The foregoing discussion is intended to illustrate that there are frequently many ways to generate an active catalyst. There are a variety of methods wherein the ligands of the present invention can be reacted with a suitable metal precursor, and optionally a co-catalyst, to generate an active olefin polymerization catalyst. Without wishing to be bound by theory, we believe that the active catalyst typically comprises the catalytically active metal, one or more ligands of the present invention, the growing polymer chain (or a hydride capable of initiating a new chain), and a site on the metal adjacent to the metal-alkyl bond of said chain where ethylene can coordinate, or at least closely approach, prior to insertion. Where specific structures for active catalysts have been implied herein, it should be understood that active catalysts comprising the ligands of the present invention are formed as the reaction products of the catalyst activation reactions disclosed herein, regardless of the detailed structures of those active species.

In some cases, it is advantageous to attach the catalyst to a solid support. Examples of useful solid supports include: inorganic oxides, such as talcs, silicas, titania, silica/chromia, silica/chromia/titania, silica/alumina, zirconia, aluminum phosphate gels, silanized silica, silica hydrogels, silica xerogels, silica aerogels, montmorillonite clay and silica co-gels, as well as organic support materials such as polystyrene and functionalized polystyrene. (See, for example, S. B. Roscoe et al., "Polyolefin Spheres from Metallocenes Supported on Non-Interacting Polystyrene," 1998, *Science*, 280, 270–273 (1998)).

Thus, in a preferred embodiment, the catalysts of the present invention are attached to a solid support (by "attached to a solid support" is meant ion paired with a component on the surface, adsorbed to the surface or covalently attached to the surface) that has been pre-treated with a compound $Y^1$. More generally, the compound $Y^1$ and the solid support can be combined in any order and any number of compound(s) $Y^1$ can be utilized. In addition, the supported catalyst thus formed may be treated with additional quantities of compound $Y^1$. In another preferred embodiment, the compounds of the present invention are attached to silica that has been pre-treated with an alkylaluminum compound $Y^1$, for example, MAO, $Et_3Al$, $^iBu_3Al$, $Et_2AlCl$, or $Me_3Al$.

Such supported catalysts are prepared by contacting the transition metal compound, in a substantially inert solvent (by which is meant a solvent which is either unreactive under the conditions of catalyst preparation, or if reactive, acts to usefully modify the catalyst activity or selectivity) with MAO-treated silica for a sufficient period of time to generate the supported catalyst. Examples of substantially inert solvents include toluene, o-difluorobenzene, mineral spirits, hexane, $CH_2Cl_2$, and $CHCl_3$.

In another preferred embodiment, the catalysts of the present invention are activated in solution under an inert atmosphere, and then adsorbed onto a silica support which has been pre-treated with a silylating agent to replace surface silanols by trialkylsilyl groups. Methods to pre-treat silicas in this way are known to those skilled in the art and may be achieved, for example, by heating the silica with hexamethyldisilazane and then removing the volatiles under vacuum. A variety of precurors and procedures may be used to generate the activated catalyst prior to said adsorption, including, for example, reaction of a (ligand)Ni(acac)B $(C_6F_5)_4$ complex with $Et_2AlCl$ in a toluene/hexane mixture under nitrogen; where "ligand" refers to a compound of the present invention.

The polymerizations may be conducted in batch or continuous processes, as solution polymerizations, as non-solvent slurry type polymerizations, as slurry polymerizations using one or more of the olefins or other solvent as the polymerization medium, or in the gas phase. One of ordinary skill in the art, with the present disclosure, would understand that the catalyst could be supported using a suitable catalyst support and methods known in the art. Substantially inert solvents, such as toluene, hydrocarbons, methylene chloride and the like, may be used. Propylene and 1-butene are excellent monomers for use in slurry-type copolymerizations and unused monomer can be flashed off and reused.

Temperature and olefin pressure have significant effects on polymer structure, composition, and molecular weight. Suitable polymerization temperatures are preferably from about 20° C. to about 160° C., more preferably 60° C. to about 100° C. Suitable polymerization pressures range from about 1 bar to 200 bar, preferably 5 bar to 50 bar, and more preferably from 10 bar to 50 bar.

The catalyst concentration in solution, or loading on a support, is adjusted to give a level of activity suitable for the process and desired polymer. In the case of solution phase or a slurry phase process using a soluble catalyst precursor, suitable catalyst concentrations are typically in the range of 0.01 to 100 micromoles/L, preferably 0.1 to 10 micromoles/L, even more preferably 0.2 to 2 micromoles/L. Higher loadings tend to reduce the solution phase concentration of ethylene at a given temperature, pressure and agitation rate, and can therefore result in relatively more chain running and branching in some cases.

In some cases, it is possible that the catalysts of the present invention may acquire new hydrocarbyl substituents, attached to the ligand or counteranion, or both, under the conditions of the olefin polymerization reaction. For example, if a bidentate N,N-donor ligand of the current invention underwent cyclometallation to form a tridentate ligand with a nickel-carbon bond, insertion of one or more ethylenes into this bond, followed by hydrogenolysis or by β-H elimnation, could result in a new hydrocarbyl side chain attached to said ligand. Alternatively, the ligand could comprise an olefinic side chain substituent prior to polymerization, and this side chain could undergo copolymerization in the presence of ethylene to attach an oligomeric or polymeric group to the ligand. It is also possible that the reaction product of (i) bis(1,5-cyclooctadiene)nickel (0), (ii) a ligand of the present invention and (iii) $B(C_6F_5)_3$ may comprise a cycloctadiene-derived hydrocarbyl bridge between cationic nickel and anionic boron, and subsequent ethylene insertion may result in the attachment of a polyethylene chain to the borate counteranion. Therefore, although hydrocarbyl groups attached to the ligand or counteranion of the current invention will generally be relatively low molecular weight groups (less than about MW=500), it is possible that they will be modified as described above under some olefin polymerization reaction conditions, and any such modified catalysts are also considered within the scope of this invention.

The catalysts of the present invention may be used alone, or in combination with one or more other Group 3–10 olefin polymerization or oligomerization catalysts, in solution, slurry, or gas phase processes. Such mixed catalysts systems are sometimes useful for the production of bimodal or multimodal molecular weight or compositional distributions, which may facilitate polymer processing or final product properties.

After the reaction has proceeded for a time sufficient to produce the desired polymers, the polymer can be recovered from the reaction mixture by routine methods of isolation and/or purification.

In general, the polymers of the present invention are useful as components of thermoset materials, as elastomers, as packaging materials, films, compatibilizing agents for polyesters and polyolefins, as a component of tackifying compositions, and as a component of adhesive materials.

High molecular weight resins are readily processed using conventional extrusion, injection molding, compression molding, and vacuum forming techniques well known in the art. Useful articles made from them include films, fibers, bottles and other containers, sheeting, molded objects and the like.

Low molecular weight resins are useful, for example, as synthetic waxes and they may be used in various wax coatings or in emulsion form. They are also particularly useful in blends with ethylene/vinyl acetate or ethylene/methyl acrylate-type copolymers in paper coating or in adhesive applications.

Although not required, typical additives used in olefin or vinyl polymers may be used in the new homopolymers and copolymers of this invention. Typical additives include pigments, colorants, titanium dioxide, carbon black, antioxidants, stabilizers, slip agents, flame retarding agents, and the like. These additives and their use in polymer systems are known per se in the art.

Other features of the invention will become apparent in the following description of working examples, which have been provided for illustration of the invention and are not intended to be limiting thereof.

The molecular weight data presented in the following examples is determined at 135° C. in 1,2,4-trichlorobenzene using refractive index detection, calibrated using narrow molecular weight distribution poly(styrene) standards.

EXAMPLES

Example 1

Synthesis of aaa1

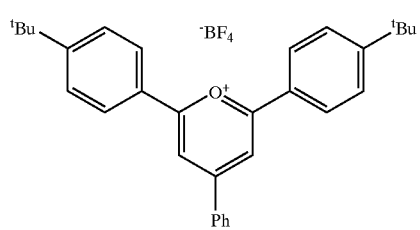

To a 500 mL round bottomed flask equipped with a magnetic stir bar was added 25 g (141.8 mmol) of 4'-tert-butylacetophenone and 7.52 g (70.9 mmol) of benzaldehyde. The solution was stirred and 20.9 mL (170.2 mmol) of boron trifluoride diethyl etherate was added dropwise. The solution was stirred for 1 h at room temperature then the reaction vessel was lowered into a preheated oil bath at 90° C. and stirred for 2 h. The reaction vessel was allowed to cool to room temperature then poured into 500 mL of diethyl ether. The product precipitated from solution and was isolated by suction filtration. The filter cake was washed with 100 mL of diethyl ether then dried under vacuum to give 11.30 g (31%) of aaa1 as a yellow solid. $^1$H NMR (DMSO-$d_6$, 300 MHz) δ 1.40 (s, 18H), 7.81 (d, J=8.8 Hz, 4H), 7.82 (m, 3H), 8.50 (d, J=8.3 Hz, 4H), 8.57 (d, J=7.7 Hz, 2H), 9.08 (s, 2H).

Example 2

Synthesis of aaa2

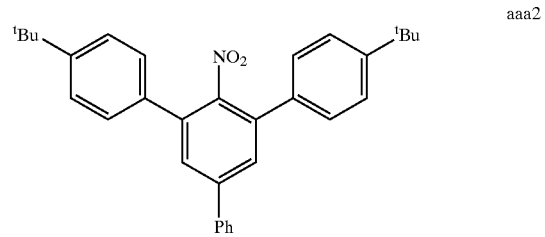

To a 500 mL round bottomed flask equipped with a magnetic stir bar and a reflux condenser was added 11.0 g (21.7 mmol) of aaa1, 100 mL of anhydrous ethanol, and 1.7 mL (32.5 mmol) of nitromethane. The mixture was stirred and 9.1 mL (65.1 mmol) of triethylamine was added over 3 minutes. The reaction vessel was lowered into a preheated oil bath at 110° C. and allowed to reflux under nitrogen. After 1 h the reaction vessel was allowed to cool to room temperature and 100 mL of methanol was added to precipitate the product. The product was collected by suction filtration, washed with 100 mL of methanol and dried under vacuum to give 6.42 g (64%) of aaa2 as a white solid. $^1$H NMR (CDCl$_3$, 300 MHz) δ 1.36 (s, 18H), 7.43 (m, 11H), 7.62 (s, 2H), 7.62 (m, 1H), 7.64 (m, 1H).

Example 3

Synthesis of aaa3

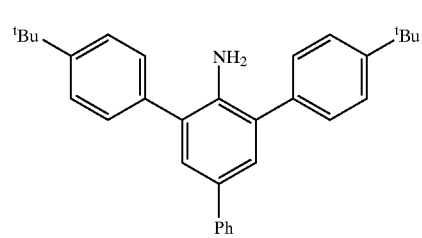

To a 300 mL Parr shaker vessel was added 6.4 g (13.8 mmol) of aaa2 and a slurry of 1.28 g of 5% Pd/C in 50 mL of DMF followed by 30 mL of methanol. The reaction vessel was purged with nitrogen three times, heated to 50° C. and shaken under 55 psi of hydrogen for 12 h. The reaction vessel was purged with nitrogen then allowed to cool to room temperature. The mixture was filtered through Celite and the Celite pad was washed with 100 ml of methylene chloride. The solution was concentrated to remove the methylene chloride then 400 mL of methanol was added to precipitate the product. The product was collected by suction filtration and washed with 100 mL of methanol to give 5.46 g (91%) of aaa3 as a white crystalline solid. $^1$H NMR (CDCl$_3$, 300 MHz) δ 1.39 (s, 18H), 3.98 (s, 2H), 7.26 (m, 2H), 7.40 (m, 4H), 7.51 (m, 7H), 7.60 (m, 2H).

Example 4

Synthesis of aaa4

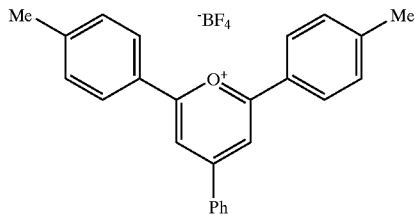

To a 500 mL round bottomed flask equipped with a magnetic stir bar was added 50 g (373 mmol) of 4'-methylacetophenone and 19.77 g (186.3 mmol) of benzaldehyde. The solution was stirred and 56.7 mL (447.12 mmol) of boron trifluoride diethyl etherate was added dropwise. The solution was stirred for 30 min at room temperature then the reaction vessel was lowered into a preheated oil bath at 90° C. and stirred for 2 h. The reaction vessel was allowed to cool to room temperature then poured into 1 L of diethyl ether. The product precipitated from solution and was isolated by suction filtration. The filter cake was washed with 500 mL of diethyl ether then dried under vacuum to give 27.85 g (35%) of aaa4 as a yellow solid. $^1$H NMR (CDCl$_3$, 300 MHz) δ 2.5 (s, 6H), 7.59 (d, J=7.9 Hz, 4H), 7.72 (m, 2H), 7.86 (m, 1H), 8.47 (d, J=8.4 Hz, 4H), 8.56 (d, J=7.3 Hz, 2H), 9.04 (s, 2H).

Example 5

Synthesis of aaa5

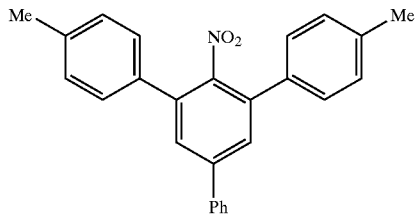

To a 300 mL round bottomed flask equipped with a magnetic stir bar and a reflux condenser was added 27.0 g (63.7 mmol) of aaa4, 100 mL of anhydrous ethanol, and 4.92 mL (95.5 mmol) of nitromethane. The mixture was stirred and 26.6 mL (191.1 mmol) of triethylamine was added. The reaction vessel was lowered into a preheated oil bath at 110° C. and allowed to reflux under nitrogen. After 2.5 h the reaction vessel was allowed to cool to room temperature and concentrated to an oil. The oil was purified by silica gel chromatography (20% methylene chloride in hexane) to give 14.93 g (62%) of aaa5 as a colorless oil that crystallized upon standing. $^1$H NMR (CDCl$_3$, 300 MHz) δ 2.41 (s, 6H), 7.26 (d, J=7.8 Hz, 4H), 7.36 (d, J=7.9 Hz, 4H), 7.46 (m, 3H), 7.61 (s, 2H), 7.64 (m, 2H).

Example 6

Synthesis of aaa6

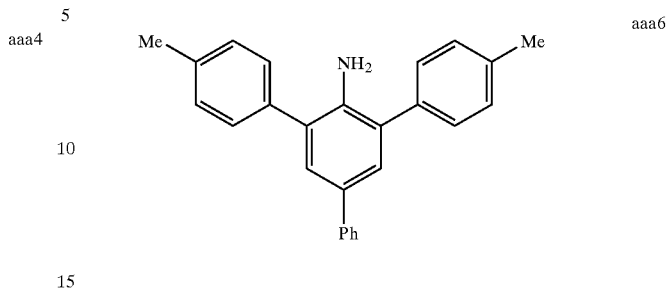

To a 300 mL Parr shaker vessel was added 17.6 g (46.4 mmol) of aaa5 and a slurry of 1.76 g of 5% Pd/C in 60 mL of DMF followed by 30 mL of methanol. The reaction vessel was purged with nitrogen three times, heated to 50° C. and shaken under 55 psi of hydrogen for 6 h. The reaction vessel was purged with nitrogen then allowed to cool to room temperature. The mixture was filtered through Celite and the Celite pad was washed with 100 ml of methylene chloride. The solution was concentrated to remove the methylene chloride then 500 mL of methanol was added to precipitate the product. The product was collected by suction filtration and washed with 100 mL of methanol to give 16.18 g (100%) of aaa6 as a white crystalline solid. $^1$H NMR (CDCl$_3$, 300 MHz) δ 2.49 (s, 6H), 3.99 (s, 2H), 7.34 (m, 1H), 7.36 (d, J=7.5 Hz, 4H), 7.44 (d, J=8.0 Hz), 7.48 (s, 2H), 7.54 (d, J=7.8 Hz, 4H), 7.67 (d, J=8.1 Hz, 2H).

Example 7

Synthesis of aaa7

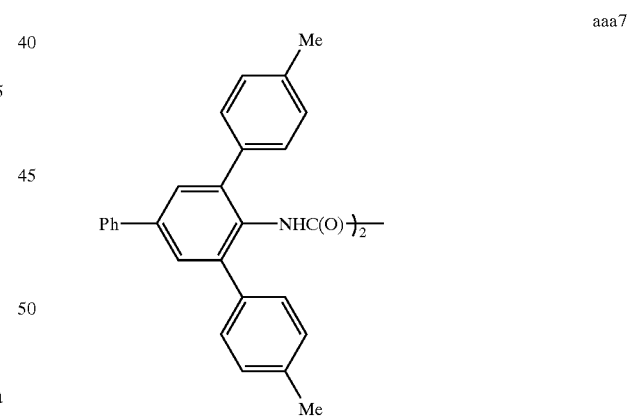

Pyridine (25 mL) was added to a 100 mL round bottomed flask equipped with a magnetic stir bar followed by 8.20 g (23.5 mmol) of aaa6. The mixture was stirred and 1.03 mL (11.75 mmol) of oxalyl chloride was added dropwise. The mixture was stirred for 2 h at room temperature then poured into 400 mL of methanol to precipitate the product. The product was isolated by suction filtration, washed with 100 mL of methanol then dried under vacuum to give 5.28 g (60%) of aaa7 as a light blue solid. $^1$H NMR (CDCl$_3$, 300 MHz) δ 2.47 (s, 12H), 7.21 (s, 16H), 7.45 (m, 6H), 7.62 (s, 4H), 7.66 (d, J=7.4 Hz, 4H), 8.71 (s, 2H).

Example 8
Synthesis of aaa8

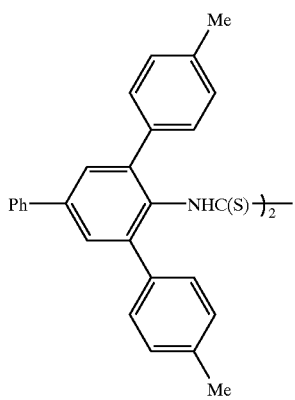

To a 250 mL round bottomed flask equipped with a magnetic stir bar was added 5.25 g (6.98 mmol) of aaa7, 100 mL of o-xylene, and 3.10 g of $P_4S_{10}$. The reaction vessel was lowered into a preheated oil bath at 150° C. and stirred under nitrogen for 1 h. The reaction vessel was allowed to cool to room temperature then poured into 400 mL of methanol to precipitate the product. The product was isolated by suction filtration then washed with 100 mL of methanol then dried under vacuum to give 5.11 g (94%) of aaa8 as orange crystals. $^1$H NMR (CDCl$_3$, 300 MHz) δ 2.44 (s, 12H), 7.13 (d, J=7.9 Hz, 8H), 7.21 (d, J=8.5 Hz, 8H), 7.41 (m, 6H), 7.61 (s, 4H), 7.65 (m, 4H), 11.2 (s, 2H).

Example 9
Synthesis of aaa9

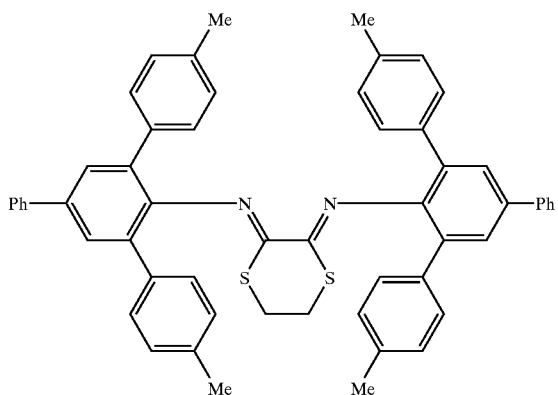

To a 100 mL round bottomed flask equipped with a magnetic stir bar was added 5.00 g (6.38 mmol) of aaa8, 10 mL of 1,2-dibromoethane, and 10 mL of 6.4 M NaOH solution followed by 409 mg (1.27 mmol) of tetrabutylammonium bromide. The mixture was stirred for 15 minutes then poured into 150 mL of methanol to give an oil that gradually solidified. The solid was isolated by suction filtration, crushed with a spatula then washed with 50 mL of methanol and dried under vacuum to give 5.14 g (100%) of aaa9 as a tan solid. $^1$H NMR (CDCl$_3$, 300 MHz) δ 2.16 (s, 4H), 2.70 (s, 12H), 7.10 (d, J=7.9 Hz, 8H), 7.42 (m, 14H), 7.62 (s, 4H), 7.69 (d, J=7.3 HZ, 4H).

Example 10
Synthesis of aaa10

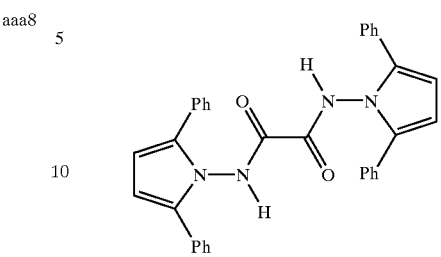

A suspension of dibenzoyl ethane (8.8 g, 37 mmol) in toluene (15 ml) and 1-methyl-2-pyrrolidinone (7.5 ml) was treated with oxalic dihydrazide (2 g, 17 mmol). The flask was fitted with a Dean Stark trap, and immersed in a 170° C. oil bath. The resulting suspension was stirred under Ar, with azeotropic removal of water until all of the starting diketone was consumed (determined by TLC), then cooled to rt. The solvent was removed in vacuo. The dark oily residue was washed with MeOH and filtered to afford a mixture (4.21 g) of N,N'-bis(2,5-diphenyl-1-pyrrolyl) oxamide contaminated with an unidentified impurity (on the order of 50–65% by weight), which was used without purification.

Example 11
Synthesis of aaa11

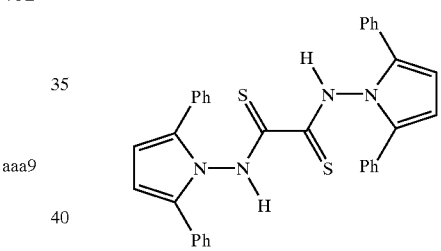

A suspension of impure aaa10 from Example 10 (523 mg) in ortho-xylene (6 ml) was treated with phosphorus pentasulfide (222 mg, 0.5 mmol). The flask was fitted with a reflux condenser, and immersed in a 180° C. oil bath. The resulting suspension was refluxed under nitrogen for ca. 2 h, then cooled to rt, then diluted with ca. 35 mL methylene chloride. The heterogeneous mixture was poured onto a column of silica (10"×50 mm) and eluted with methylene chloride/toluene (3/2), collecting only the forerunning orange-red band. The solvent was removed in vacuo to give aaa11 as deep violet needles (yield 121 mg).

Example 12
Synthesis of aaa12

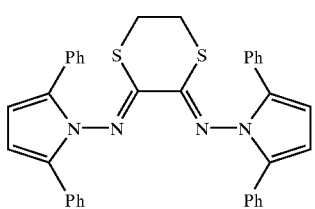

A suspension of aaa11 (566 mg, 1.02 mmol) in 1,2-dibromoethane (7 ml) was treated with tetrabutylammonium bromide (15 mg) and 2 N aq NaOH (10 mL). The biphasic mixture was stirred vigorously for 15 min. The color discharged markedly and a pale precipitate separated almost immediately on stirring. The mixture was diluted with methylene chloride (200 mL) and water (200 mL). The layers were separated, and the organic layer was washed with water (2×50 mL) and dried ($MgSO_4$), concentrated, and adsorbed onto silica, then chromatographed over silica eluting with methylene chloride/hexane. The solvent was removed in vacuo to give aaa12 as an orange-yellow powder (yield 520 mg).

Example 13

Synthesis of aaa13

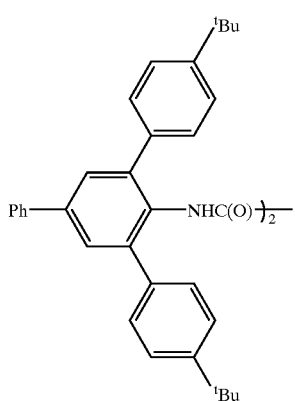

aaa13 aaa3 (5.1 g, 11.76 mmol) was dissolved in pyridine (5 mL) and treated with 4-(dimethylamino)-pyridine (30 mg). Under an atmosphere of dry nitrogen gas, oxalyl chloride (515 mL, 5.88 mmol) was added dropwise. The mixture was stirred ca. 72 h at rt, then heated to 60 C for 2 h more. After cooling to rt, tlc analysis indicated that some of the aniline remained unreacted, but the desired product was the major component of the reaction mixture. The reaction mixture was treated with methanol to precipitate the desired product. The white powder was collected by vacuum filtration, and washed with methanol to afford 4.4 g aaa13.

Example 14

Synthesis of aaa14

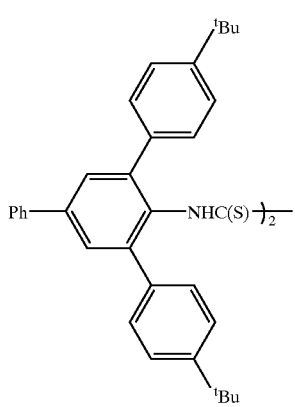

aaa14

A suspension of aaa13 (4.4 g, 4.78 mmol) in ortho-xylene (20 ml) was treated with phosphorus pentasulfide (1.1 g, 2.39 mmol). The flask was fitted with a reflux condenser, and immersed in a 180° C. oil bath. The resulting suspension was refluxed under nitrogen for ca. 3 h, then cooled to rt, then diluted with ca. 35 mL methylene chloride. The heterogeneous mixture was poured onto a column of silica (10"×50 mm) and eluted with methylene chloride/hexane, collecting only the forerunning orange band. Upon concentration, aaa14 crystallized from solution as orange needles (2 g), and was collected by filtration. The filtrate was concentrated to give more aaa14 as an orange crystalline powder (1.8 g).

Example 15

Synthesis of aaa15

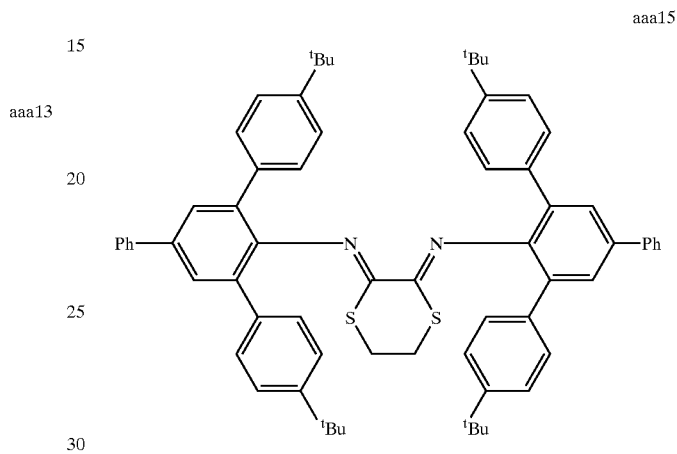

aaa15

A suspension of aaa14 (2 g, 2.1 mmol) in 1,2-dibromoethane (7 ml) was treated with tetrabutylammonium bromide (15 mg) and 2 N aq NaOH (10 mL). The biphasic mixture was stirred vigorously for 1.5 h. The color discharged markedly and a pale precipitate separated. The mixture was diluted with methylene chloride (200 mL) and water (200 mL). The layers were separated, and the organic layer was washed with water (2×50 mL). The organic layer was concentrated to 50 mL, the treated with methanol. aaa15 crystallized as short pale yellow needles (1.19 g, $1^{st}$ crop). A second crop eventually crystallized from the filtrate (0.66 g). A third crop was obtained by treating the filtrate of the second with a few mLs of water (110 mg).

Example 16

Synthesis of bbb1

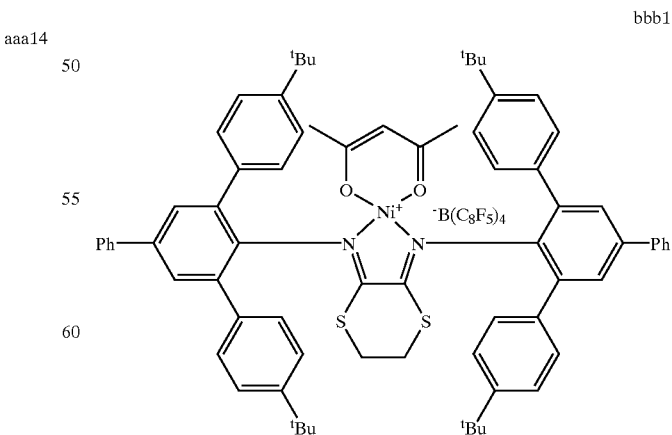

bbb1

In an argon filled glove box, aaa15, (98.0 mg, 0.100 mmol), nickel(II)acetonylacetonate (25.7 mg, 0.100 mmol), and triphenylcarbenium tetrakis(pentafluorophenyl)borate (92.3 mg, 0.100 mmol) were weighed to a Schlenk flask. On the Schlenk line, 10 mL dry diethyl ether was added to give a dark red solution. Dry hexane (4 mL) was added and dark crystals separated. The supernatant was removed via filer paper-tipped cannula. The dark bronze crystals were washed (2×10 mL) with a hexane/ether (1/1) mixture, then dried several hours in vacuo to afford 163.3 mg (89%) bbb1.

Example 17
Synthesis of bbb2

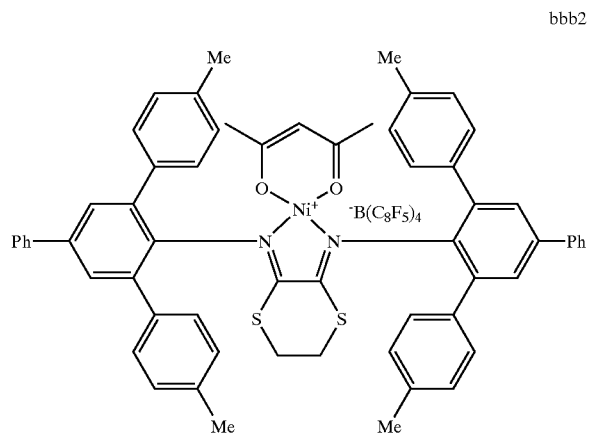

bbb2

Ligand aaa9 (1.00 g) was treated with nickel(II) acetonylacetonate and triphenylcarbenium tetrakis (pentafluorophenyl)borate according to the procedure given in Example 16 to afford 1.71 g (84%) bbb2.

Example 18
Preparation of a Heterogeneous Catalyst Comprising Ligand a54

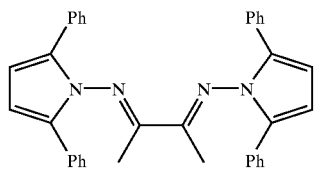

a54

To a vial charged with a54 (23 mg; 44 μmol), Ni(acac)$_2$ (12.8 mg; 49.8 μmol) and Ph$_3$CB(C$_6$F$_5$)$_4$ (46.2 mg; 50 μmol) was added 0.8 mL dichloromethane. The resulting solution was stirred for a few hours and subsequently added dropwise to silica (0.5 g; Grace Davison Sylopol 2100). Volatiles were then removed under vacuum to give the desired product.

Example 19
Polymerization of Ethylene Using the Catalyst Prepared in Example 18

A catalyst delivery device was charged with the catalyst prepared in Example 18 (2.5 mg; 0.19 μmol Ni, dispersed in 130 mg Grace Davison XPO-2402 silica) and fixed to the head of a 1000-mL Parr® reactor. The device was placed under vacuum. The reactor was then charged with NaCl (298 g) that had been dried in vacuum at 130° C. for several hours, closed, evacuated and backfilled with nitrogen five times. The leak rate of the reactor was tested by pressurizing to ca. 200 psi C$_2$H$_4$ for 5 min. The reactor was then depressurized, and the salt treated with trimethylaluminum (10 mL; 2.0 M in hexane) and agitated at 75° C. for 30 min. The reactor was subsequently pressurized with ethylene (200 psi) and depressurized to atmospheric pressure three times. The catalyst was then introduced in the reactor with appropriate agitation. The reaction was allowed to proceed for 60 min at 75° C. The reactor was then depressurized. The polymer was isolated by washing the content of the reactor with hot water. The isolated polymer was further treated with 6 M HCl in methanol, rinsed with methanol and dried under vacuum to give 5.72 g (1,000,000 TO; 2240 g polymer/g catalyst; GPC: M$_n$=65,400, M$_w$/M$_n$=3.4; $^1$H NMR: 10 BP/1000C; T$_m$=122° C.).

Example 20
Preparation of a Heterogeneous Catalyst Comprising Ligand aa1

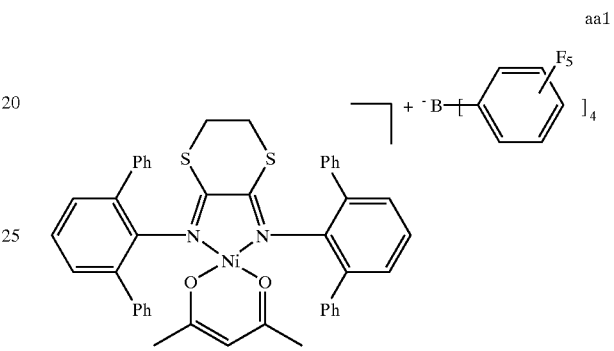

aa1

A solution of aa1 (73.6 mg) was dissolved in 0.75 mL dichloromethane and added dropwise to 0.50 g silica (Grace Davison XPO-2402). The volatiles were removed in vacuo (1.5 h) at room temperature. The resulting solid was used as such in subsequent polymerizations.

Example 21
Polymerization of Ethylene Using the Catalyst Prepared in Example 20

A catalyst delivery device was charged with the catalyst prepared in Example 20 (3.8 mg; 0.33 μmol Ni) dispersed in 122 mg silica (Grace Davison XPO-2402) and fixed to the head of a 1000-mL Parr® reactor. The device was placed under vacuum. The reactor was then charged with NaCl (315 g) that had been dried in vacuum at 130° C. for several hours, closed, evacuated and backfilled with nitrogen five times. The leak rate of the reactor was tested by pressurizing to ca. 200 psi C$_2$H$_4$ for ca. 5 min. The reactor was then depressurized, and the salt treated with trimethylaluminum (10 mL; 2.0 M in hexane) and agitated at 86° C. for 30 min. The reactor was subsequently pressurized with ethylene (200 psi) and depressurized to atmospheric pressure three times. The catalyst was then introduced in the reactor with appropriate agitation. The reaction was allowed to proceed for 240 min at 90 C. The reactor was then depressurized. The polymer was isolated by washing the content of the reactor with hot water. The isolated polymer was further treated with 6 M HCl in methanol, rinsed with methanol and dried under vacuum to give 8.1 g (850,000 TO; 2100 g polymer/g catalyst; GPC: partially insoluble; $^1$H NMR: 11.7 BP/1000C; T$_m$=111.2 C).

Example 22
Polymerization of Ethylene Using the Catalyst Prepared in Example 20, with Hydrogen as a Chain-transfer Agent A catalyst delivery device was charged with the catalyst prepared in Example 20 (3.8 mg; 0.33 μmol Ni) dispersed in 122 mg silica (Grace Davison XPO-2402) and fixed to the head of a 1000-mL Parr® reactor. The device was placed under vacuum. The reactor was then charged with NaCl (372 g) that had been dried in vacuum at 130° C. for several hours, closed, evacuated and backfilled with nitrogen five times. The salt was then treated with trimethylaluminum (10 mL; 2.0 M in hexane) and agitated at 85° C. for 30 min. The reactor was subsequently pressurized with ethylene (200 psi) and depressurized to atmospheric pressure three times. The catalyst was then introduced in the reactor with appropriate agitation. The reaction was allowed to proceed for 30 min at 85 C. The reactor was then depressurized and hydrogen (100 mL) was added via syringe. The reactor was then repressurized with ethylene (200 psi) and the reaction allowed to proceed for an additional 210 min. The reactor was depressurized to atmospheric pressure. The polymer was isolated by washing the content of the reactor with hot water. The resulting polymer was further treated with 6 M HCl in methanol, rinsed with methanol and dried under vacuum to give 4.41 g (278,000 TO; 686 g polymer/g catalyst; GPC: $M_n$=70,100, $M_w$=589,000. (The chromatogram was bimodal with $M_p$=2,700,000 and 200,000.)

Example 23
Polymerization of Ethylene Using the Catalyst Prepared in Example 20, with Hydrogen as a Chain-transfer Agent A catalyst delivery device was charged with the catalyst prepared in Example 20 (14.9 mg; 1.3 µmol Ni) dispersed in 152 mg silica (Grace Davison XPO-2402) and fixed to the head of a 1000-mL Parr® reactor. The device was placed under vacuum. The reactor was then charged with NaCl (363 g) that had been dried in vacuum at 130° C. for several hours, closed, evacuated and backfilled with nitrogen five times. The salt was then treated with trimethylaluminum (10 mL; 2.0 M in hexane) and agitated at 85° C. for 30 min. The reactor was subsequently pressurized with ethylene (200 psi) and depressurized to atmospheric pressure three times. Hydrogen (100 mL) was then syringed in the reactor and the reactor subsequently repressurized to 600 psi ethylene as the catalyst was introduced in the reactor with appropriate agitation. The reaction was allowed to proceed for 30 min at 89° C. The reactor was then depressurized to atmospheric pressure. The polymer was isolated by washing the content of the reactor with hot water. The resulting polymer was further treated with 6 M HCl in methanol, rinsed with methanol and dried under vacuum to give 26.2 g (1,300,000 TO; 1750 g polymer/g catalyst; GPC: $M_n$=179,000, $M_w$=717,000).

Example 24
Preparation of a Tethered Catalyst Derived from Ligand aaa16

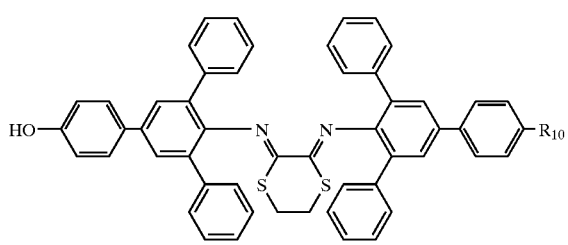

aaa16

$Ph_3CB(C_6F_5)_4$ (14.5 mg; 15.7 µmol) was added to a solution of aaa16 (12.6 mg; 16.0 µmol, prepared by methods similar to those described above, from the 2,6-diphenyl-4-(4-methoxyphenyl)-aniline, with the methoxy group being de-O-methylated as the last step) and $Ni(acac)_2$ (4.1 mg; 16 µmol) in acetone to result in a Ni concentration of 9.4 µmol/mL. An aliquot (0.75 mL) of the resulting solution was collected and the volatiles removed in vacuo. The residue was taken up in 1.0 mL dichloromethane, resulting in a Ni concentration of 7.1 µmol/mL. To an aliquot of this solution (0.70 mL; 5.0 µmol) was added tetramethyldisilazane (5.3 µmol) and further diluted with dichloromethane to afford 6.4 µmol/mL. A volume of this solution, equivalent to 1.9 µmol Ni, was diluted with dichloromethane to reach a concentration of 3.33 µmol/mL. The resulting solution was then added dropwise to silica (381 mg; Grace Davison XPO-2402). The resulting solid was stored at room temperature for several hours (ca. 18 h) prior to adding toluene (50 mL). The mixture was stirred for 60 min and the supernatant removed with a cannula equipped with a filter. The residual solid was further washed with toluene (2×25 mL) and then dried in vacuo to give an orange solid, used as such in subsequent polymerization experiments.

Example 25
Polymerization of Ethylene Using the Catalyst Prepared in Example 24

A 600-mL Parr® reactor was charged with the catalyst prepared in Example 24. Toluene (150 mL) was added to the reactor before pressurizing to 200 psi ethylene to saturate the mixture. The reactor was then depressurized and MMAO type 4 (1.5 mL; 7.14 wt % Al; Akzo Nobel) was added. The reactor was repressurized with ethylene (200 psi) and the temperature quickly ramped up to 85° C. The reaction was allowed to proceed under those conditions for 120 min before being quenched by addition of methanol. The mixture was treated with 6M HCl. The polymer was collected by filtration and dried in a vacuum oven to give 1.43 g (38 g polyethylene/g catalyst; GPC: $M_n$=1,033,000, $M_w$=2,354,000; $^1$H NMR: 12.7 BP/1000 C; $T_m$=114.7° C.).

Example 26
Ethylene Polymerization with the Nickel Catalyst Derived from $Ni(acac)_2$, $B(C_6F_5)_3$, $Ph_3C(C_6F_5)_4$ and Ligand a52

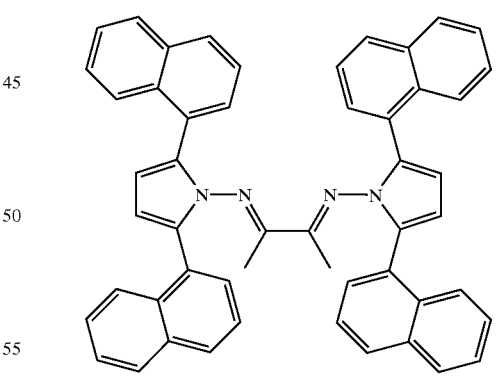

a52

A 1 L Parr® autoclave, Model 4520, was dried by heating under vacuum to 180 C at 0.6 torr for 1 h, then cooled and refilled with dry nitrogen. The autoclave was charged with dry, deoxygenated hexane (450 mL) and 4.0 mL of a 10 wt % solution of MMAO (modified methylalumoxane; 23% iso-butylaluminoxane in heptane; 6.42% Al). The reactor was sealed and heated to 80° C. under nitrogen, then sufficient hydrogen was added to raise the pressure by 15.5 psi, after which sufficient ethylene was introduced to raise the total pressure to 300 psig. A sample loop injector was first purged with 2.0 mL dry, deoxygenated dichloromethane (injected into the reactor), and then used to inject 2.0 mL of a stock solution (corresponding to 0.60 μmol of pro-catalyst) prepared from 17.09 mL of CH$_2$Cl$_2$ and 2.91 mL of a stock solution prepared from 42 mg ligand a52, 10.1 mg Ni(acac)$_2$, 20.0 mg B(C$_6$F$_5$)$_3$, 36 mg Ph$_3$C(C$_6$F$_5$)$_4$ and a total of 23.964 g CH$_2$Cl$_2$ (with the 1$^{st}$ three reagents being combined in CH$_2$Cl$_2$ and then added to a solution of the trityl salt in CH$_2$Cl$_2$), followed by 2.0 mL of CH2Cl2, using ethylene gas to force the liquids into the autoclave and raise the pressure to ca. 440 psig, after which time the reactor was isolated and the pressure was allowed to fall to about 370 psig. More ethylene was then reintroduced to raise the pressure back to ca. 440 psig, and the cycle was repeated. A second injection of 2.0 mL of the same stock solution of pro-catalyst (corresponding to another 0.60 μmol) was made at 17.5 min. The average pressure was 402 psig, and the average temperature was 80.4° C. After 100 min, the reaction was quenched by injection of MeOH, then the reactor was cooled, depressurized and opened. The polyethylene precipitate was recovered by filtration and dried in vacuo to obtain 50.6 g white polyethylene. A similar experiment without hydrogen, conducted for 80 min, gave 32.92 g polyethylene.

Example 27
Ethylene Polymerization with bbb1

A procedure similar to that described in Example 26 was followed, using 450 mL hexane, 4.0 mL MMAO, 14.0 psig hydrogen, sufficient ethylene pressure to give 660 psig total pressure, a reaction temperature of 100° C., a single injection of 0.6 μmol of bbb1 in CH$_2$Cl$_2$ solution, and a reaction time of 58 min to obtain 27.0 g polyethylene, corresponding to 1.61 (10)$^6$ mol C2H4/mol Ni.

Example 28
Polymerization of Ethylene Using the Catalyst Prepared in Example 20, with Hydrogen as a Chain-transfer Agent A catalyst delivery device was charged with the catalyst prepared in Example 20 (7.0 mg; 0.61 μmol Ni) dispersed in 160 mg silica (Grace Davison XPO-2402) and fixed to the head of a 1000-mL Parr® reactor. The device was placed under vacuum. The reactor was then charged with NaCl (324 g) that had been dried in vacuum at 130° C. for several hours, closed, evacuated and backfilled with nitrogen five times. The salt was then treated with trimethylaluminum (10 mL; 2.0 M in hexane) and agitated at 85° C. for 30 min. The reactor was subsequently pressurized with ethylene (200 psi) and depressurized to atmospheric pressure three times. Hydrogen (100 mL) was added to the reactor via a syringe. The catalyst was then introduced in the reactor with appropriate agitation. The reaction was allowed to proceed for 30 min at 85° C. The reactor was depressurized to atmospheric pressure. The polymer was isolated by washing the content of the reactor with hot water. The resulting polymer was further treated with 6 M HCl in methanol, rinsed with methanol and dried under vacuum to give 0.67 g (30,000 TO; 73 g polymer/g catalyst; GPC: M$_n$=127,400, M$_w$=463,000; 13.9 BP/1000 C by $^1$H NMR).

Example 29
Polymerization of Ethylene Using the Catalyst Prepared in Example 20, with Hydrogen as a Chain-transfer Agent A catalyst delivery device was charged with the catalyst prepared in Example 20 (5.5 mg; 0.48 μmol Ni) dispersed in 148 mg silica (Grace Davison XPO-2402) and fixed to the head of a 1000-mL Parr® reactor. The device was placed under vacuum. The reactor was then charged with NaCl (350 g) that had been dried in vacuum at 130° C. for several hours, closed, evacuated and backfilled with nitrogen five times. The salt was then treated with trimethylaluminum (10 mL; 2.0 M in hexane) and agitated at 85° C. for 30 min. The reactor was subsequently pressurized with ethylene (200 psi) and depressurized to atmospheric pressure three times. The catalyst was then introduced in the reactor with appropriate agitation. The reaction was allowed to proceed for 3 min at 85° C. under 200 psi ethylene. The reactor was then depressurized and hydrogen (100 mL) was syringed in. The reactor was then repressurized with ethylene (200 psi) and the reaction allowed to proceed for a total reaction time of 120 min. The reactor was depressurized to atmospheric pressure. The polymer was isolated by washing the content of the reactor with hot water. The resulting polymer was further treated with 6 M HCl in methanol, rinsed with methanol and dried under vacuum to give 2.0 g (140,000 TO; 340 g polymer/g catalyst; GPC: M$_n$=81,600 M$_w$=301,800; 12.4 BP/1000 C by $^1$H NMR; T$_m$ (by DSC)=122.2° C.).

Example 30
Ethylene Polymerization with the Nickel Catalyst Derived from Ni(acac)$_2$, B(C$_6$F$_5$)$_3$, Ph$_3$C(C$_6$F$_5$)$_4$ and Ligand v22

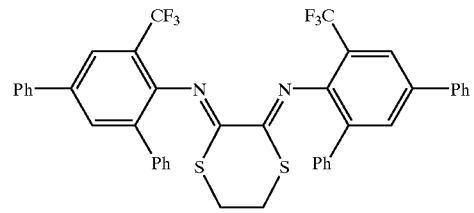

A 1 L Parr® autoclave, Model 4520, was dried by heating under vacuum to 180° C. at 0.6 torr for 1 h, then cooled and refilled with dry nitrogen. The autoclave was charged with dry, deoxygenated hexane (450 mL) and 2.0 mL of a 0.25 M solution of triisobutylaluminum in hexanes. The reactor was sealed and heated to 80° C. under nitrogen, then sufficient hydrogen was added to raise the pressure by 8.9 psi, after which sufficient ethylene was introduced to raise the total pressure to 250 psig. A sample loop injector was first purged with 2.0 mL dry, deoxygenated dichloromethane (injected into the reactor), and then used to inject 3×2.0 mL of a stock solution (corresponding to a toal of 3.0 μmol of pro-catalyst) prepared from 17.34 mL of CH$_2$Cl$_2$ and 2.66 mL of a stock solution prepared from 45.3 mg ligand v22, 15.0 mg Ni(acac)$_2$, 54 mg Ph$_3$C(C$_6$F$_5$)$_4$ and a total of 19.546 g (14.75 mL) CH$_2$Cl$_2$, followed by 2.0 mL of CH$_2$Cl$_2$, using ethylene gas to force the liquids into the autoclave and raise the pressure to ca. 440 psig, after which time the reactor was isolated and the pressure was allowed to fall to about 380 psig. More ethylene was then reintroduced to raise the pressure back to ca. 440 psig, and the cycle was repeated throughout the experiment to give an average pressure of 404 psig, and an average temperature was 80.4° C. After 52 min, the reaction was quenched by injection of MeOH, then the reactor was cooled, depressurized and opened. The polyethylene was recovered by concentrating the mixture to dryness under vacuum to obtain 13.01 g amorphous polyethylene.

Example 31

The procedure of Example 30 was followed without change, except the average temperature was 60.1° C., the average pressure was 605 psig, the partial pressure of hydrogen was 4.49 psi, and the total reaction time was 59.7 min. This afforded 38.6 g amorphous polyethylene, corresponding to 460,000 mol ethylene/mol nickel.

Example 32
Preparation of a Compound of Formula kk1

Bis(thioamide) aaa14 is reacted with 1 equivalent of $Bu_2Sn(OSO_2CF_3)_2$ and 2 equivalents of a non-nucleophilic base, such as 2,4,6-tri-tert-butylpyridine to afford a compound of formula kk1, with $M^1L_n=Bu_2Sn$, and $Ar^{2a}=Ar^{2b}=$ 2,6-di(4-tert-butylphenyl)-4-phenylphenyl. Alternatively, bis(thioamide) aaa14 is reacted with 1 equivalent of $Cp_2Zr(NMe_2)_2$ to afford a compound of formula kk1, with $M^1L_n=Cp_2Zr$, and $Ar^{2a}=Ar^{2b}=$2,6-di(4-tert-butylphenyl)-4-phenylphenyl.

Example 33
Preparation of a Compound of Formula kk2

2 equivalents of bis(thioamide) aaa14 are reacted with 1 equivalent of $SnCl_4$ or $TiCl_4$ and 4 equivalents of a non-nucleophilic base, such as 2,4,6-tri-tert-butylpyridine to afford a compound of formula kk2, with $M^1L_n=Sn$ or Ti, and $Ar^{2a}=Ar^{2b}=$2,6-di(4-tert-butylphenyl)-4-phenylphenyl. Alternatively, 2 equivalents of bis(thioamide) aaa14 are reacted with 1 equivalent of $Ti(NMe_2)_4$ to afford a compound of formula kk2, with $M^1L_n=Ti$, and $Ar^{2a}=Ar^{2b}=$2,6-di(4-tert-butylphenyl)-4-phenylphenyl.

We claim:

1. A compound of formula ii1;

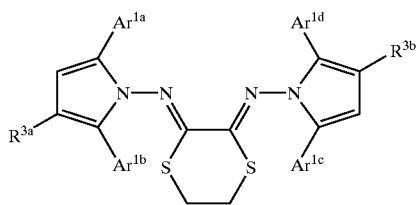

ii1 wherein:

$R^{3a,b}$ are each independently H, methyl, phenyl, 4-methoxyphenyl, or 4-tert-butylphenyl; and $Ar^{1a-d}$ are each independently phenyl, 4-methylphenyl, 4-tert-butylphenyl, 4-trifluoromethylphenyl, 1-naphthyl, 2-naphthyl, or 4-phenylphenyl.

2. A compound selected from Set 21;

Set 21

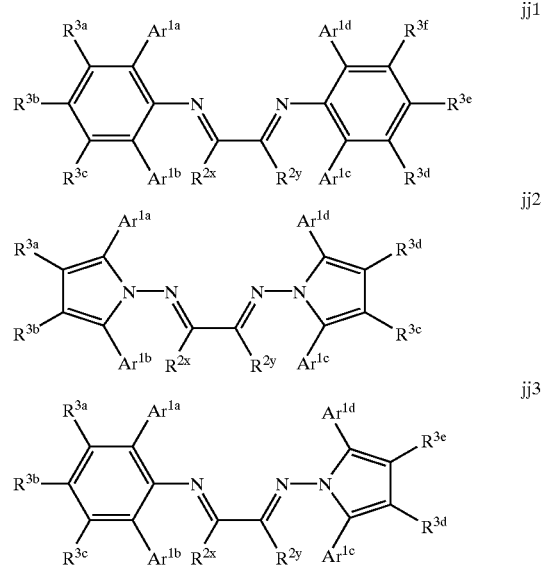

wherein:

$R^{2x,y}$ are each independently H, hydrocarbyl, substituted hydrocarbyl, heteroatom connected hydrocarbyl, or heteroatom connected substituted hydrocarbyl; in addition, $R^{2x}$ and $R^{2y}$ may be linked by a bridging group;

$R^{3a-f}$ are each independently H, alkyl, hydrocarbyl, substituted hydrocarbyl, heteroatom connected hydrocarbyl, heteroatom connected substituted hydrocarbyl, or fluoroalkyl; and $Ar^{1a-d}$ are each independently phenyl, 4-alkylphenyl, 4-tert-butylphenyl, 4-trifluoromethylphenyl, 4-hydroxyphenyl, 4-(heteroatom attached hydrocarbyl)-phenyl, 4-(heteroatom attached substituted hydrocarbyl)-phenyl, 1-naphthyl, 2-naphthyl, 9-anthracenyl, or aryl.

* * * * *